(12) United States Patent
Pizzo et al.

(10) Patent No.: US 6,403,092 B1
(45) Date of Patent: Jun. 11, 2002

(54) IMMUNE RESPONSE MODULATOR ALPHA-2 MACROGLOBULIN COMPLEX

(75) Inventors: Salvatore Pizzo, Bahama; Hanne Grøn, Chapel Hill, both of NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/282,826

(22) Filed: Mar. 31, 1999

Related U.S. Application Data

(63) Continuation-in-part of application No. 09/053,301, filed on Apr. 1, 1998, now abandoned.

(51) Int. Cl.$^7$ .................. A61K 39/12; A61K 39/35; A61K 39/385; A61K 39/39; A61K 48/00
(52) U.S. Cl. .................. 424/183.1; 424/186.1; 424/188.1; 424/189.1; 424/195.11; 424/196.11; 424/208.1; 424/227.1; 530/402; 530/403
(58) Field of Search .................. 424/186.1, 188.1, 424/189.1, 195.11, 196.11, 208.1, 227.1, 185.1; 530/403, 402

(56) References Cited

U.S. PATENT DOCUMENTS 5,057,414 A 10/1991 Stief

FOREIGN PATENT DOCUMENTS

WO WO 94/14976 7/1994

OTHER PUBLICATIONS

Chu et al., 1994, J. Immunol. 152:1538–45.
Chaudhuri, 1993, Indian J. Exp. Bio. 31:723–7.
Borth et al., 1989, J. Biol. Chem., 264:5818–25.
Barrett et al, 1973, Biochem J, 133:709.
Borth et al., 1973, Biochem J. 133:529–39.
Borth et al., 1990, Blood 75:2388–95.
Borth, 1992, FASEB J. 6:3345–53.
Bolton et al, 1973, Biochem J, 133:529–39.
Bury, 1981, J Chromatogr, 213:491.
Canfield, 1963, J Biol Chem, 238:2691.
Chu et al, 1991, Biochemistry, 30:1551.
Chu et al, 1993, J Immunol, 150:48.
Chu, et al, 1994, Lab Invest, 71:792–812.
Feldman et al, 1985, Proc Natl Acad Sci USA, 82:5700.
Gettins et al, 1994, Ann NY Acad Sci, 737:383–98.
Gontijo et al, 1991, J Immunol, 34:577.
Gron et al, 1996, Biochem J, 318:539–45.
Gron et al, 1998, Biochem, 37:6009–14.
Hall et al, 1978, Biochem J, 171:27.
Hart et al, 1991, Proc Natl Acad Sci USA, 88:9448–52.
Herz et al, 1988, EMBO J, 7:4119.
Howard et al, 1995, J Clin Invest, 97:1193–1203.
Imber et al, 1981, J Biol Chem, 256:8134.
Ito et al, 1984, Mol Cell Endocrin, 36:165.
James, 1980, Trends Biochem Sci, 5:43.
Kawamura et al, 1986, J Immunol, 136:58.
Lanzavecchia, 1990, Semin in Immunol, 4:275.
Lorenz et al, 1990, J Immunol, 144:1600.
Manca et al, J Exp Med, 173:37.
Misra et al, 1993, Biochem J, 290–885.
Mitsuda et al., Biochem. Biophys. Res. Comm. 194(3):1155–60.
Mitsuda et al., Biochem. Biophys. Res. Comm. 191(3):1326–31
Osada et al., 1988, Biochem. Biophys. Res. Comm. 150:883–9.
Osada et al., 1987, Biochem. Biophys. Res. Comm. 143:954–8.
Osada et al., 1987, Biochem. Biophys. Res. Comm. 146:26–31.
Osada et al, 1987, Biochem Biophys Res Com, 142:100–6.
Pizzo et al, 1984, in The Receptor, vol. 1, Conns ed. Academic Press, Orlando FL, p177.
Praissan et al, 1968, Biochemistry, 7:2431–45.
Quigley et al., Ann. New York Acad. Sci. 712:131–145.
Rock et al, 1984, J Exp Med, 160:1102.
Salvesen et al, 1980, Biochem J, 187:695.
Salvesen et al, 1981, Biochem J, 195:453–61.
Salvesen et al, Methods Enzymol, 223:121.
Sottrup–Jensen, 1987, in The Plasma Proteins: Structure, Function, and Genetic Control, vol. V Putnams ed. Academic Press, Inc. Orlando, FL, p191.
Stockinger, 1992, Eur J Immunol, 22:1271.
Su et al, 1989, Immunology, 66:466.
Swenson et al, 1979, Proc Natl Acad Sci USA, 76:4313–6.
Unanue, 1981, Adv Immunol, 31:1–136.
Van Leuven et al, 1982, Biochem J, 201:119–28.
Webb et al., (1995) Eur. J. Biochem. 234:714–22.

*Primary Examiner*—David Saunders
*Assistant Examiner*—Mary Beth Tung
(74) *Attorney, Agent, or Firm*—Klauber & Jackson

(57) ABSTRACT

Activation of $\alpha_2$-macroglobulin ($\alpha_2$M) with a nucleophilic compound followed by incubation of the activated $\alpha_2$M at elevated temperature with a biomolecule results in covalent incorporation of the intact biomolecule into the $\alpha_2$M molecule, without the use of proteinases. The thus-formed structurally defined and stable complex may be used as an antigen for stimulating the immune response, for example, in the form of a vaccine. Enhanced antigen presentation of a particular biomolecule is provided, especially for those that are poorly immunogenic; reduction of the immunodominance of particular epitopes is also provided.

63 Claims, 13 Drawing Sheets

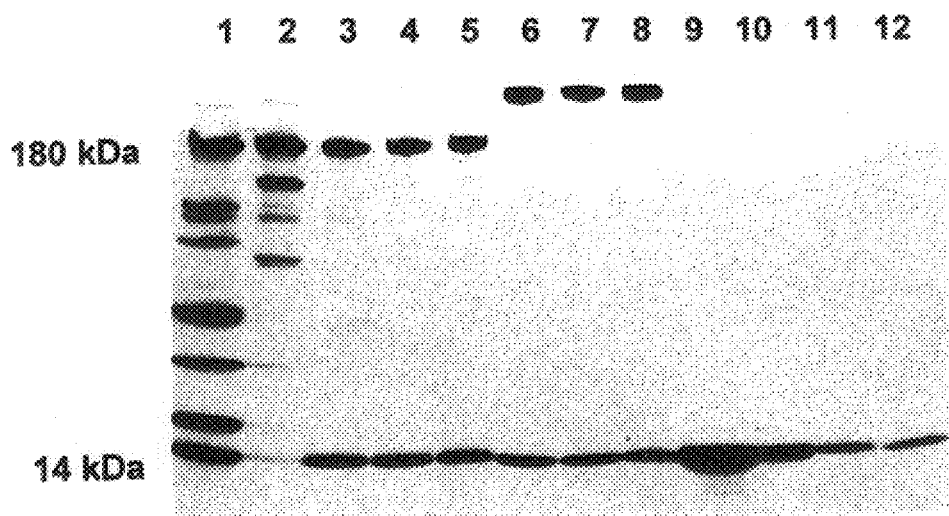
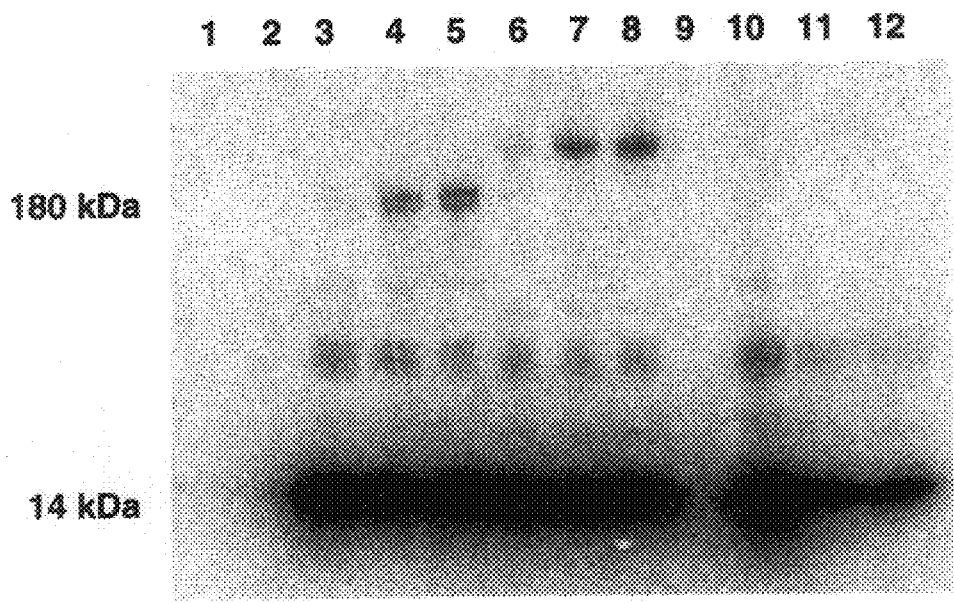

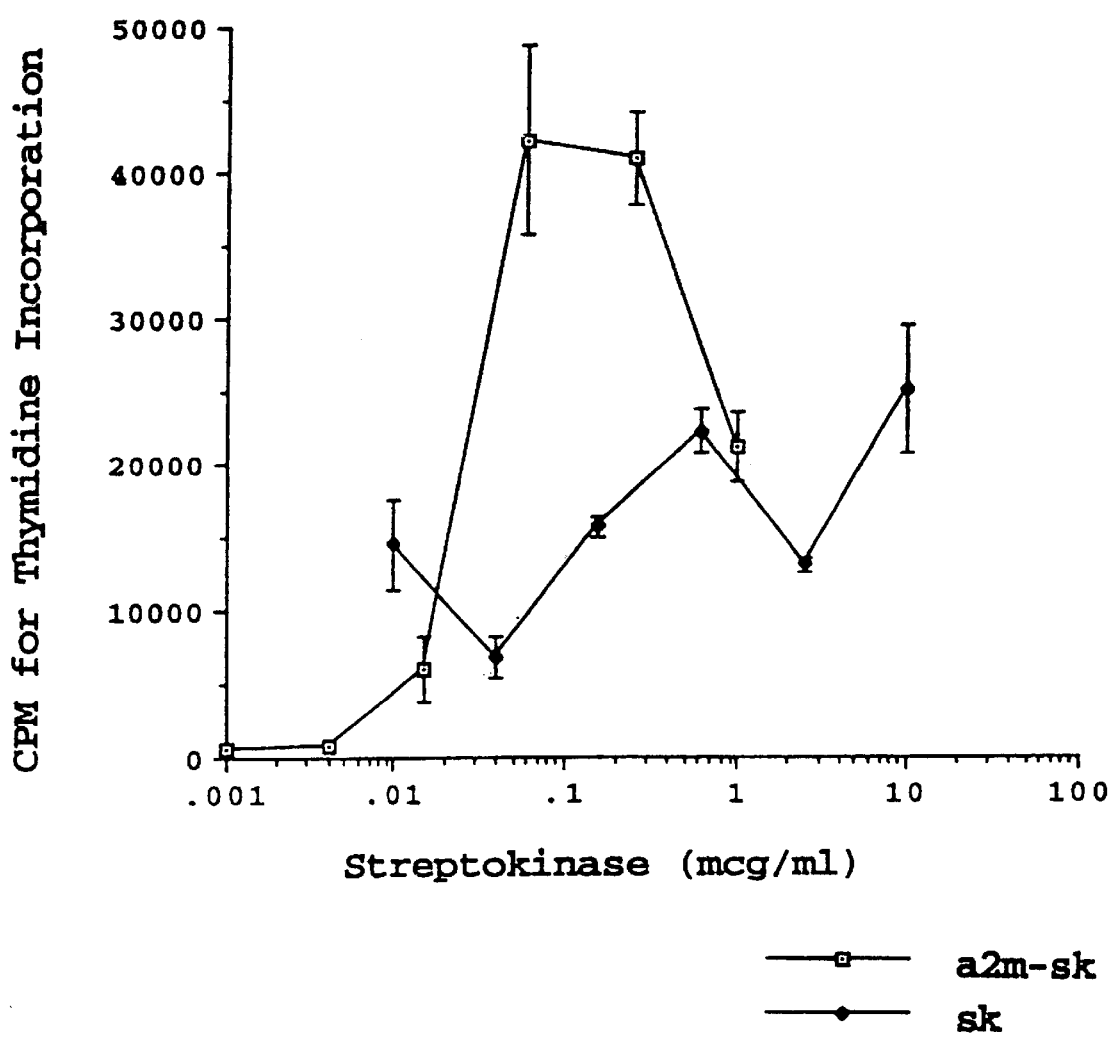

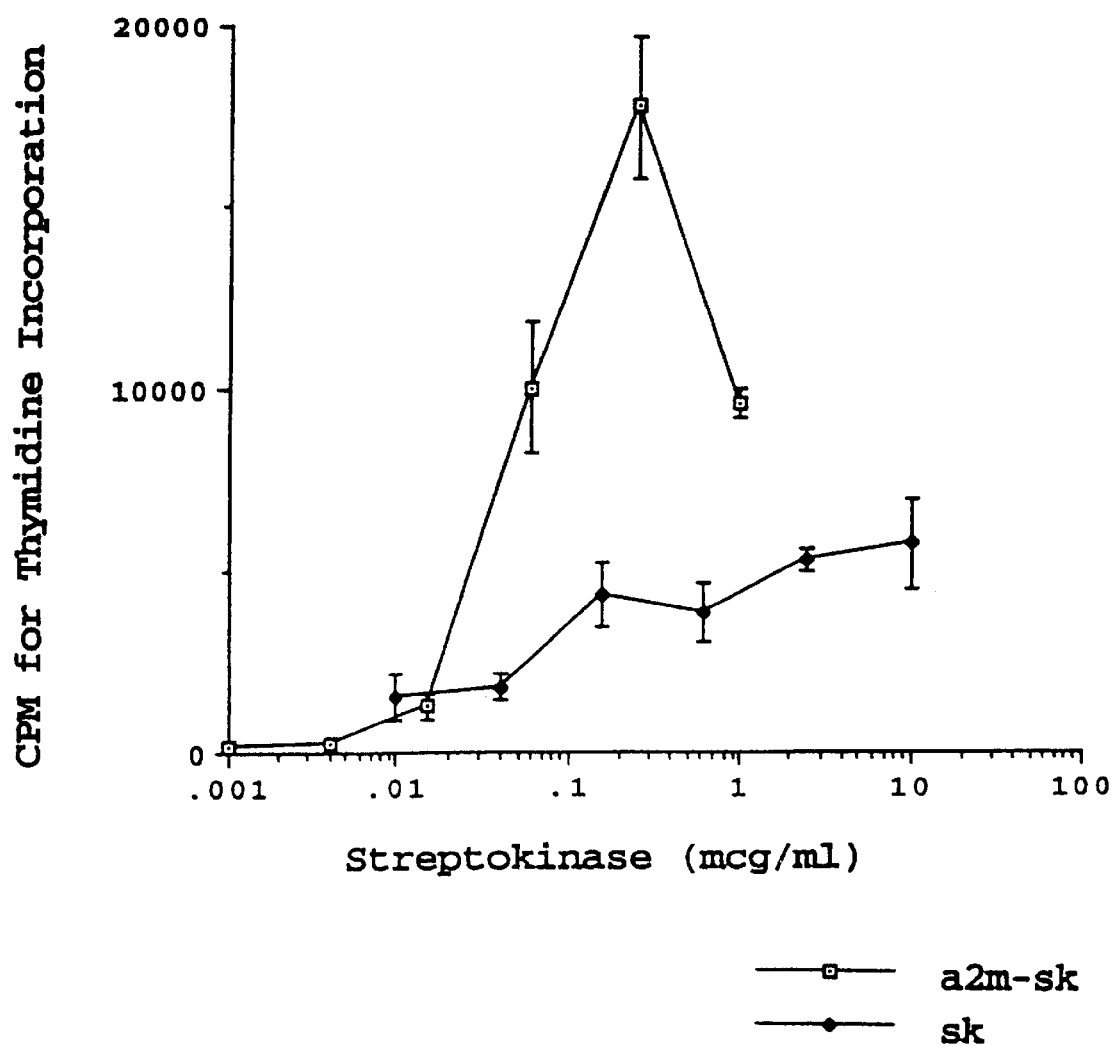

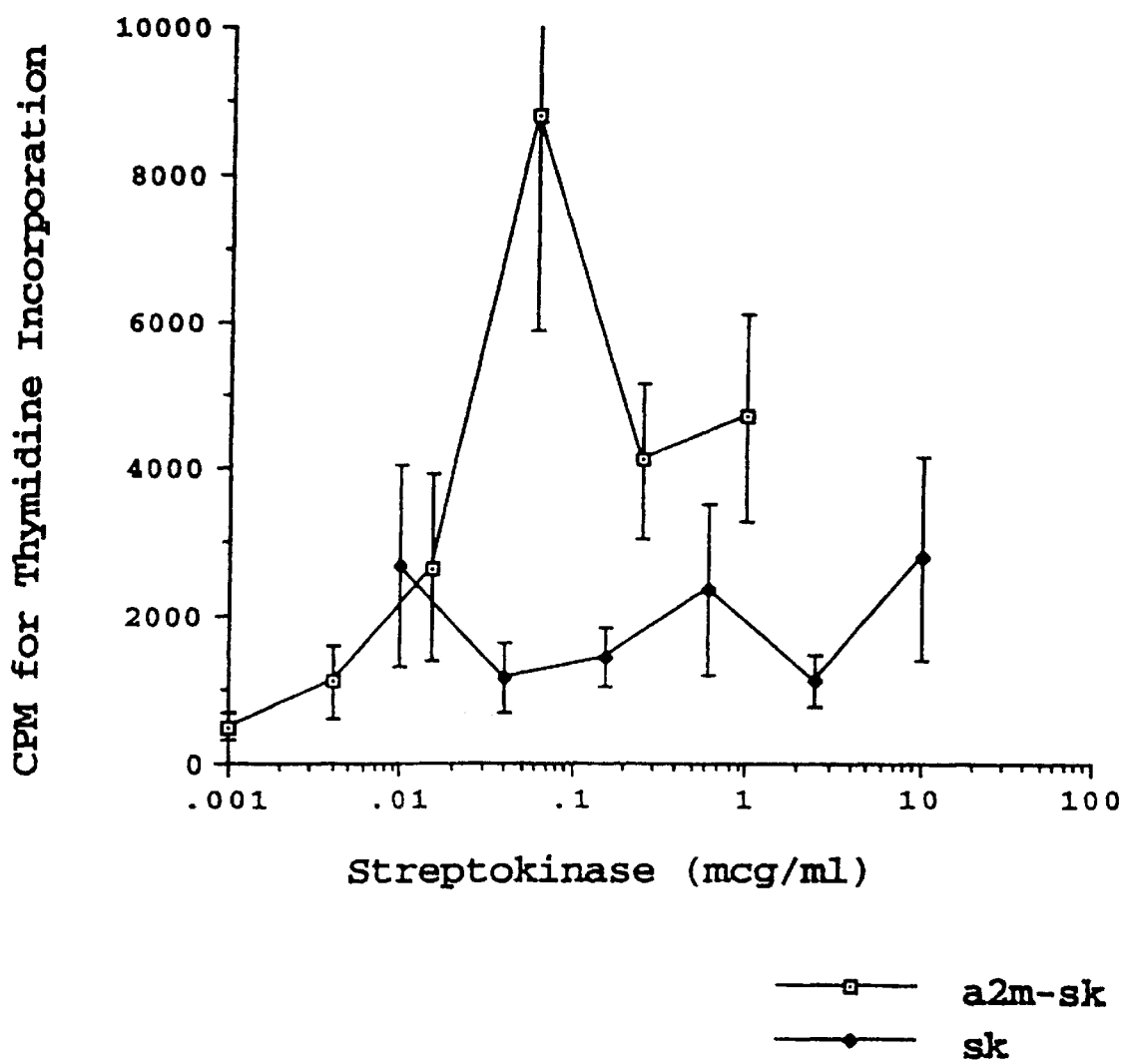

IMMUNE RESPONSE MODULATOR ALPHA-2 MACROGLOBULIN COMPLEX

RELATED APPLICATION DATA

This Application is a Continuation-In-Part of Ser. No. 09/053,301, filed Apr. 1, 1998 now abandoned.

The research leading to the present invention was funded in part by Grant Nos. HL-24066 and CA-29589 from the National Institutes of Health, and Danish Research Council Grant No. 11-0529-1. The government may have certain rights in the invention.

TECHNICAL FIELD OF THE INVENTION

The present invention relates generally to the field of immunology and, more particularly, to antigen-$\alpha_2$-macroglobulin complexes, the facile and reproducible preparation of antigen-$\alpha_2$-macroglobulin complexes, and their subsequent uses, including the enhancement of host immunocompetence and the preparation and administration of vaccines for prevention and treatment of disease states.

BACKGROUND OF THE INVENTION

Antigen Presentation and Immunogenicity

In general, antigens are "presented" to the immune system by antigen presenting cells (APCs), including, for instance, macrophages, dendritic cells and B-cells in the context of major histocompatibility complex molecules (MHCs) which are present on the APC surface. Normally, natural antigens and molecules supplied as immunogens are thought to be taken up and partially digested by the APCs, so that smaller pieces of the original antigen are then expressed on the cell surface in the context of MHC molecules.

It is also presently understood that T-lymphocytes, in contrast to B-lymphocytes, are relatively unable to interact with soluble antigen. Typically T-lymphocytes require antigen to be processed and then expressed on the cell surface of APCs in the context of MHC molecules as noted above. Thus, T-cells, and more particularly, the so called "T-cell receptors," are able to recognize the antigen in the form of a bimolecular ligand composed of the processed antigen and one or more MHC molecules. In addition to presenting antigens on MHC molecules, the APC must be activated to express co-stimulatory molecules, such as B7/B1, before effective stimulation of T-cells can occur.

Many epitopes on proteins, including both foreign and endogenous proteins, are generally unrecognized or only weakly recognized by the immune system. These epitopes therefore elicit little or no antibody or other immune response, or at most, only a weak response. It has therefore been difficult, and in some instances, impossible to raise antibodies against such epitopes. In contrast, other epitopes elicit extraordinarily strong immune responses, in some instances, to the exclusion (or partial exclusion) of other epitopes within the same antigen molecule. Such epitopes can be termed "immunodominant."

A separate problem arises in the preparation and administration of vaccines, and particularly vaccines that present peptide antigens. Traditional methods for preparing such vaccines that present antigens as macromolecules through conjugation to protein carriers or polymerization are often unable to induce cytotoxic T lymphocytes (CTL) response in vivo. In such instances an adjuvant is usually added. Use of an adjuvant in the immunizing protocol has the advantage of enhancing the humoral response but has mixed results in priming specific CTL response. Unfortunately, popular adjuvants used in laboratory animals, such as Freund's complete adjuvant, are too toxic and unacceptable for humans. Ideally, protection against viral infection is best provided by both humoral and cell-mediated immunities, including long-term memory and cytotoxic T cells.

For example, the human immunodeficiency virus (HIV), the etiologic agent most closely associated with the acquired immunodeficiency syndrome (AIDS), has become an important objective for various vaccine developments. The predominant vaccine strategy has focused on the use of the envelope protein antigens gp120 and gp160 of HIV-1 produced by recombinant DNA technology. However, the full promise of their use in vaccines cannot presently be realized unless they are administered along with an effective adjuvant.

Enhanced Antigen Presentation

The targeting of antigen (abbreviated Ag) to APC has been extensively studied in vitro and in vivo [For review see (1, 2)]. Techniques that have been used include encapsulating Ag into liposomes (3, 4), crosslinking Ag to antibodies directed against surface proteins (5–9), and forming immune complexes for recognition by FcR (10). A complementary approach of decorating B cell surfaces with mAb recognizing a particular Ag also conferred enhanced ability to present that Ag (11). The capacity for Ag uptake by different APC appears to correlate with efficiency of presentation (12), although Ag focusing or intracellular signaling may also contribute. In general, targeting of Ag to the APC surfaces appears to enhance the immune response.

While B-cells possess specific receptors, surface Ig, for capturing the Ag they present efficiently (13,14), macrophages and other non-B cell APCs must utilize other mechanisms. These may include phagocytosis of particulate or cellular Ag and enhanced endocytosis of opsonized Ag or immune complexes. Yet, the efficient uptake and presentation of soluble Ag by these non-B cell APCs in naive animals is not fully understood. A receptor-mediated process might be involved.

Among the APCs, the macrophages are of particular interest by virtue of the central role that they play in the regulation of the activities of other cells of the immune system. Macrophages act as effector cells in microbial and tumor cell killing as well, and are believed to secrete numerous cytokines that orchestrate many of the diverse aspects of the immune response. The ability of macrophage to regulate a range of immunologic events is in part a function of their expression of Ia surface antigens. The expression of membrane Ia antigens is essential for the induction of specific T cell responses to antigens (15).

The effective internalization and processing of diverse proteins forms a central issue in antigen presentation by macrophages. The immune system must balance the capacity for interacting with vast numbers of dissimilar molecules with the requirements for efficiently responding to very low amounts of Ag. Although macrophages are able to sample their environments through pinocytosis, a need for more efficient means of internalization, such as a receptor-mediated system, has been suggested (16). The targeting of Ag to surface receptors on macrophages or B-cells, either by artificial crosslinking or by exploiting membrane Ig, enhances the efficiency of presentation (1,16,17); however, a naturally occurring antigen presentation system in macrophages has not yet been identified.

The α-Macroglobulin Family of Proteins

The α-macroglobulins and the complement components C3, C4, and C5 comprise a superfamily of structurally related proteins. The α-macroglobulin family includes proteinase-binding globulins of both $α_1$ and $α_2$ mobilities. The most extensively studied α-macroglobulin is human $α_2$-macroglobulin ($α_2M$), a large tetrameric protein capable of covalently binding other proteins (19–27) and targeting them to cells bearing the $α_2M$ receptor (27–30). Although size and charge may affect the extent of binding, $α_2M$ can incorporate proteins bearing nucleophilic amino acid side chains in a relatively non-selective manner. This rapid covalent linking reaction is restricted, however, to a window of time initiated by proteinase-induced conformational change, during which an internal thioester on each subunit becomes susceptible to nucleophilic substitution (20,21,31). Thus, $α_2M$, C3 and C4 are evolutionarily-related thioester-containing proteins that undergo conformational and functional changes upon limited proteolysis (32,33), resulting in possible formation of thioester-mediated covalent bonds with targets such as proteinases, cell-surface carbohydrates or immune complexes, respectively.

Human $α_2$-macroglobulin ($α_2M$) is an abundant protein in plasma (2–5 mg/ml). It consists of four identical subunits arranged to form a double-sided molecular "trap" (34). This trap is sprung when proteolytic cleavage within a highly susceptible stretch of amino acids, the "bait region," initiates an electrophoretically detectable conformational change that entraps the proteinase (35). The resulting receptor-recognized $α_2M$ is efficiently internalized by macrophages, dendritic cells, and other cells that express $α_2M$ receptors [reviewed in (36); see also (37)], one of which has recently been cloned and sequenced (38, 39). Reaction of $α_2M$ with methylamine results in a similar conformational change to a receptor-recognized form of $α_2M$. Methylamine-treated and proteinase-treated $α_2M$ are equivalent with regard to binding, internalization and signaling. Amine-treated or protease-treated $α_2$-macroglobulin is termed $α_2$-macroglobulin* and abbreviated $α_2M^*$. Receptor-recognized α-macroglobulins from different animal species cross-react with similar affinities for the $α_2M$ receptor regardless of the proteinase used [See (36,40,41) for review]. The additional binding of non-proteolytic proteins does not appear to affect the rate of internalization even when artificial crosslinking is employed (28,29,42). Therefore, regardless of the mechanism of binding, proteins complexed with $α_2M^*$ can be effectively internalized.

The possible role of $α_2$-macroglobulin as a delivery vehicle for antigens, hormones or enzymes has been reviewed previously in the art (43–47). In the past, there have been numerous other studies suggesting a role for $α_2M$ in immune modulation (Reviewed in (48)).

Antigen-$α_2$-macroglobulin Complex Formation

As described above and in the cited literature, antigens which are not themselves proteinases are unable to become covalently bound to $α_2$-macroglobulin by co-incubation of the antigen with $α_2$-macroglobulin. Covalent incorporation of a potential antigen into the $α_2$-macroglobulin molecule requires the participation of a proteolytic enzyme to cleave the $α_2$-macroglobulin molecule as a necessary precursor step to then permit its thiol ester to react with and thus bind the antigen. While the use of a proteolytic enzyme allows the in-vitro preparation of the desired antigen-$α_2$-macroglobulin complex, the requirement for a proteolytic enzyme in this process is significantly deleterious to the structural and epitopic integrity of the antigen desired to be complexed with $α_2$-macroglobulin, as it may be proteolyzed into smaller fragments during the preparation of the complex or after it has bound to the $α_2$-macroglobulin. Furthermore, the proteolytic enzyme itself is always incorporated into the complex, thus imposing steric hindrance limiting the size of the antigen that is incorporated into $α_2M$ to about 40 kilodaltons. Thus, the facile and reproducible preparation of a complex between $α_2$-macroglobulin and an antigen of any size for the purpose of, for example, using the complex as a vaccine, is not straightforward. The structure of the antigen may be materially altered by proteolytic cleavage, and the extent and purity of antigen and other components incorporated into the $α_2$-macroglobulin may affect the quality and quantity of final complex formed.

Other means for preparing antigen-$α_2$-macroglobulin complexes are also not straightforward. Treatment of $α_2$-macroglobulin with a low molecular weight amine (nucleophile) to cleave the thiol ester achieves the conversion to the desired receptor-recognized form of $α_2$-macroglobulin; however, the amine-modified thiol ester is no longer able to bind antigen at the glutamyl residue of the thioester. Several investigators have evaluated whether amine-treated (e.g., methylamine-treated) $α_2$-macroglobulin has the capability of binding an antigen, including proteinases. No covalent linking of trypsin or elastase was seen when methylamine-treated $α_2M$ was incubated with these enzymes for several hours at 23° C. (49, 50). Thus, preparation of a covalent antigen-$α_2M^*$ complex in the absence of proteinase was heretofore unachievable.

A need therefore exists for the development of a simple and reproducible method for the preparation of a covalent complex between $α_2$-macroglobulin and a desired antigen without limitation to size, avoiding the use of proteolytic enzymes and reproducibly providing a vaccine or other material in which the antigen is stable and structurally defined for use in modulating the immune response. It is towards these goals that the present invention is directed.

SUMMARY OF THE INVENTION

The invention described herein relates generally to the modulation of the immune response by a structurally-defined and stable antigen covalently coupled to the receptor-recognized form of $α_2$-macroglobulin ($α_2M^*$). The antigen-$α_2$-macroglobulin complex of the present invention comprises a covalent adduct of the antigen and $α_2$-macroglobulin with an intact bait region, the antigen incorporated into the amine-activated form of $α_2$-macroglobulin by nucleophilic exchange in the absence of proteolytic enzymes. The antigen may be covalently bound to the glutamyl or cysteinyl residues of the cleaved thiol ester of the $α_2$-macroglobulin molecule, or it may be bound to both. One or more antigens may be bound to the complex. More particularly, the present invention is directed towards facile and reproducible methods of preparing the covalent complex between the antigen and the receptor-recognized form of $α_2$-macroglobulin in which conditions for the preparation of the complex do not compromise the integrity of the antigen. The complex prepared by the procedures described herein provide a stable and defined material for use as a vaccine or other reagent for modulating immunocompetence in an animal or in an in vitro system. The size of the coupled antigen is not limited. Furthermore, the complexes described herein may be used for increasing the immune response to an otherwise poorly immunogenic antigen, and, under certain conditions, for the suppression of the immune response to a particular antigen.

In contrast to the prior art antigen-$α_2$-macroglobulin* complexes, and procedures for preparing such complexes, whereby coupling is achieved by the concomitant use of a proteolytic enzyme to cleave $\alpha_2$-macroglobulin and to render the thiol ester available for reaction with an antigen, in the practice of the present invention, the antigen is coupled to a previously nucleophile-activated $\alpha_2$-macroglobulin, in the absence of proteolytic enzymes, using an elevated temperature and correspondingly-appropriate duration of incubation to achieve the desired coupling. Thus, the $\alpha_2$-macroglobulin in the complex of the present invention has an intact bait region. $\alpha_2$-Macroglobulin first may be activated by a low molecular weight amine such as ammonia, methylamine, ethylamine, propylamine and the like. Ammonia and methylamine are preferred. The antigen may be incubated with the amine-activated $\alpha_2$-macroglobulin at a temperature of from about 35 C. to 55 C., and for an appropriate duration to achieve the desired coupling. Selection of the appropriate temperature may be made depending on the stability of the particular antigen. For example, at 50° C., coupling may be achieved in 1–5 hour; at 37° C., the coupling may be achieved at 24 hours. Preferred conditions for an antigen stable at 50° C. is 1–5 hours. Preferred conditions for an antigen stable at 37° C. is 24 hours.

The $\alpha_2$-macroglobulin used in the present invention be native protein or that produced recombinantly, using well known techniques in molecular biology.

Suitable antigens for coupling to $\alpha_2$-macroglobulin to prepare the complexes of the present invention include nucleophiles, and extend to and include peptides, proteins, carbohydrates, cytokines, growth factors, hormones, enzymes, toxins, nucleic acids such as anti-sense RNA, as well as other drugs or oligonucleotides.

In a further embodiment, the antigen may be mildly oxidized, for example, by N-chlorobenzenesulfonamide, to increase the amount of antigen coupled to $\alpha_2$-macroglobulin by the methods of the present invention.

The complex formed by the procedure of the present invention may be introduced to a cell culture system or host animal, or to a target tissue or organ, where it is believed that $\alpha_2 M^*$ augments presentation of the desired antigen and the development of the corresponding immune response will occur.

One of the advantages of the present invention and a particular feature thereof, resides in the fact that the complex prepared by the covalent binding of $\alpha_2 M$ to a given antigen by the procedures described herein, can be administered as a vaccine without need for an adjuvant. In view of the difficulties that are experienced when adjuvant formulations are included in vaccines, the preparation of vaccines in accordance with the present invention represents a significant improvement and offers the promise of a far more efficient vehicle for antigen presentation, and one which will avoid many of the drawbacks such as toxicity and the like that are experienced with current adjuvant-containing formulations.

Also, the complexes of the present invention have particular utility in their affinity for macrophages, and other cells that bind or internalize $\alpha_2 M$. The scope of antigens, immunogens or immune modulating molecules that may be associated in the complex of the present invention is equally diverse, as it extends from oligonucleotides, proteins, peptides, cytokines, toxins, enzymes, growth factors, antisense RNA and drugs, to other carbohydrates that may exhibit some desired modulatory effect on the target cells. There is a need only for a nucleophilic group, such as an amine, sulfhydryl, or hydroxyl, to exchange with the amine present on $\alpha_2$-macroglobulin*. The invention is therefore contemplated to extend to these variations within its spirit and scope.

A further advantage of the invention is that it provides for independently targeting a receptor-binding $\alpha 2M$, as well as complexes of the invention comprising these components, for endocytosis or for cell signaling and activation. Proper activation of the APC is necessary for effective antigen presentation and effective stimulation of the immune response in general.

It is contemplated that both positive and negative regulation of the antigenicity of epitopes can be achieved. For example, by rendering epitopes recognized, or recognizable, antibodies can be raised to recognize and bind to the antigen. Enhanced antigenicity and the ability to raise antibodies to otherwise weak, scarce or ineffective epitopes finds great utility not only, for example, in vaccine applications in animals, including humans, but also in producing antibodies which can be used as reagents for, among other uses, binding, identifying, characterizing and precipitating epitopes and antigens, such as the production of antibodies against scarce antigens for research purposes. Preferably, the immunogenicity of a given antigen is enhanced according to the methods of the invention.

Alternatively, this invention contemplates the down regulation or suppression of immune responses to immunodominant epitopes, by the preferential stimulation of immune responses to otherwise "subordinate" epitopes, or by the introduction of agents or factors that on presentation, would selectively suppress the immunogenicity of the target epitope. This additional ability to modulate antigenicity may be useful, for example, in immunizing animals, including humans, and also in producing antibodies which are reactive towards otherwise silent or weakly antigenic epitopes. Such antibodies are also useful for, among other things, binding, identifying, characterizing and precipitating epitopes and antigens in vivo and in vitro.

The invention described herein also preferably includes the antibodies produced by the methods described herein or in response to the immunogens, prepared as described herein, said antibodies including monoclonal, polyclonal and chimeric antibodies, as well as immortal strains of cells which produce such antibodies, for example hybridomas which produce monoclonal antibodies which recognize the molecules and other antigens of interest. Advantageously, such antibodies can be prepared against epitopes on the antigen that are normally secondary or even suppressed.

The invention also encompasses cellular immune system components, e.g., T-lymphocytes raised in response to such antigens or immunogens, pharmaceutical compositions containing the antigens, antibodies or cellular immune system components and various methods of use.

The invention provides for enhancing the efficiency of immunizations. This can have useful application not only for potential therapeutic interventions, in particular vaccinations, but also for production of antibodies or primed lymphocytes (T or B) against scarce antigens for research purposes.

Accordingly, it is a principal object of the present invention to provide a structurally defined and stable complex of an antigen with $\alpha_2$-macroglobulin for the purposes described herein.

It is another object of the invention to provide a stable complex comprising one or more intact biomolecules and activated $\alpha_2$-macroglobulin, in which each of the biomolecules is covalently bound to an amino acid residue of the cleaved thiol ester of $\alpha_2$-macroglobulin. The biomolecule may be bound to the glutamyl residue, or to the cysteinyl residue, or to both residues. The biomolecule may be a peptide, protein, carbohydrate, cytokine, growth factor, hormone, enzyme, toxin, anti-sense RNA, a therapeutic drug, an oligonucleotide, lipid, DNA, an antigen, an immunogen, or an allergens. The biomolecule may have a molecular weight of between about 0.5 and 100 kilodaltons.

It is another object of the invention to provide an immunogen that comprises an antigenic molecule having at least one epitope in a complex with $\alpha_2$-macroglobulin. The immunogen is a complex prepared by the sequential steps of activating $\alpha_2$-macroglobulin by incubation with a nucleophilic compound to form nucleophile-activated $\alpha_2$-macroglobulin, removing the excess nucleophilic compounds, and incubating the nucleophile-activated $\alpha_2$-macroglobulin with the biomolecule.

It is yet another object of the present invention to provide a method for the preparation of a covalent complex between one or more intact biomolecules and $\alpha_2$-macroglobulin by carrying out the steps of 1) activating said $\alpha_2$-macroglobulin by incubation with a nucleophilic compound to form nucleophile-activated $\alpha_2$-macroglobulin; 2) removing excess nucleophilic compound; and 3) incubating the nucleophile-activated $\alpha_2$-macroglobulin with said biomolecule.

It is yet a further object of the present invention to provide an immunogen which comprises an antigenic molecule in a complex with $\alpha_2$-macroglobulin, wherein the antigenic molecule has at least one epitope, and in which the $\alpha_2$-macroglobulin is capable of binding a receptor for $\alpha_2$-macroglobulin. In another embodiment, a method of rendering a poorly immunogenic epitope on an antigen recognizable by the immune system by preparing a complex between reacting said antigen molecule with $\alpha_2$-macroglobulin, exposing an antigen presenting cell having major histocompatibility complex to the complex; and contacting said antigen presenting cell with lymphocytes.

It is still a further object of the present invention to provide a vaccine which comprises an antigen-$\alpha_2$-macroglobulin complex prepared by the methods herein. In a further embodiment, a method of producing T-lymphocytes which recognize an antigen is described which comprises administering to a mammal a T-lymphocyte priming effective amount of a complex comprising an antigen and $\alpha_2$-macroglobulin prepared in accordance with the present invention, which is capable of binding a receptor for $\alpha_2$-macroglobulin; and harvesting said T-lymphocytes from the mammal. In a still further embodiment, a method of treating or preventing an infectious disease, an autoimmune disease or cancer in a mammalian patient in need of such treatment or prevention is described, comprising administering to the patient an effective amount of an immunogen comprised of a complex comprising an antigen and $\alpha_2$-macroglobulin in accordance with the present invention, which $\alpha_2$-macroglobulin is capable of binding a receptor for $\alpha_2$-macroglobulin, in an amount effective for modifying the immune response to said antigen.

It is a further object of the present invention to provide a method for the preparation a structurally defined and stable complexes of particular antigens with $\alpha_2$-macroglobulin which may be carried out easily and reproducibly for the various uses herein.

It is a still further object of the present invention to provide a method for the preparation of corresponding complexes as aforesaid that facilitate improved immune recognition and activation.

It is a still further object of the present invention to provide a method and corresponding complexes as aforesaid that can be used to selectively activate epitopes in distinction to other immunodominant epitopes.

It is a still further object of the present invention to provide a method for the facile development of clinically significant amount of antibodies directed against scarce antigens.

Other objects and advantages will become apparent to those skilled in the art from a review of the ensuing detailed description which proceeds with reference to the following illustrative drawings.

BRIEF DESCRIPTION OF THE DRAWINGS

FIG. 4 depicts an electrophoretic analysis of the complex prepared at 37° C. by incubating Bolton-Hunter labeled lysozyme and $NH_3$-treated $\alpha_2$M*. At the indicated times, aliquots were frozen to be analyzed for electrophoretic mobility by 4–20% SDS PAGE (A) and PHOSPHORIMAGER™ scanning (B). The sample concentrations were not corrected for precipitation after prolonged exposure to 37° C. The lanes are as follows: 1, molecular weight marker; 2, native $\alpha_2$M; 3–5, reduced $\alpha_2$M* incubated with Bolton-Hunter labeled lysozyme for 0 h, 5 h and 24 h, respectively; 6–8, non-reduced $\alpha_2$M* incubated with Bolton-Hunter labeled lysozyme for 0 h, 5 h and 24 h, respectively; 9, reduced 16 µg non-labeled lysozyme; 10, reduced 4 µg Bolton-Hunter labeled lysozyme; 11, reduced 0.8 µg Bolton-Hunter labeled lysozyme; 12, non-reduced 0.8 µg Bolton-Hunter labeled lysozyme.

FIG. 8 depicts the incorporation of $^3$H-thymidine into peripheral blood mononuclear cells from individual SW five days after exposure of cells to a range of doses of a complex of streptokinase and $\alpha_2$-macroglobulin (open squares) prepared in accordance with the method of the present invention, in comparison with streptokinase alone (closed diamonds).

FIG. 9 depicts the same experiment as described for FIG. 8 with cells from individual HG.

FIG. 10 depicts the same experiment as described for FIG. 8 with cells from individual KW.

DETAILED DESCRIPTION OF THE INVENTION

Figure 1A:
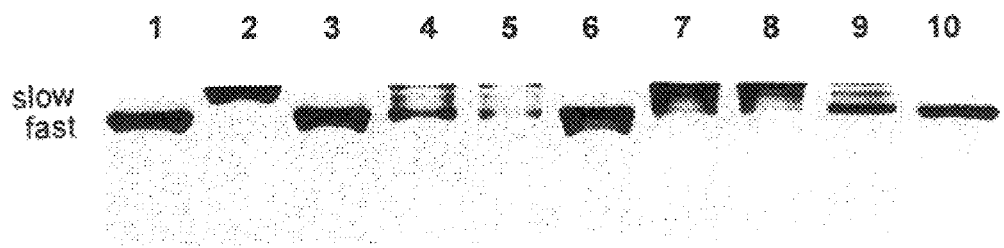
FIG. 1 depicts the electrophoretic analysis of a complex of $^{125}$I-Bolton-Hunter labeled hen egg lysozyme and $\alpha_2$M* formed at 50° C. The complex was prepared at 50° C. by incubating Bolton-Hunter labeled lysozyme and $NH_3$-treated $\alpha_2$M* as described in the Example 1. At the indicated times, aliquots were frozen to be analyzed for electrophoretic mobility by non-denaturing 4–15% pore-limit PAGE (A) and PHOSPHORIMAGER™ scanning (B). After 5 h of incubation an aliquot was gel-filtrated, and the $\alpha_2$M-containing fractions pooled (lanes 9 and 10). The sample concentrations were not corrected for precipitation after prolonged exposure at 50° C. The lanes are as follows: 1, "fast" migrating $\alpha_2$M*; 2, "slow" migrating $\alpha_2$M; 3–5, $\alpha_2$M* incubated with $^{125}$I-Bolton-Hunter labeled lysozyme at 50° C. for 0 h, 5 h and 24 h, respectively; 6–8, $\alpha_2$M* alone incubated at 50° C. for 0 h, 5 h and 24 h, respectively; 9, isolated $\alpha_2$M*-lysozyme complex; 10, isolated $\alpha_2$M*-Iysozyme complex, treated with porcine pancreatic elastase.

The following terms and abbreviations are used herein, and have the following meanings unless otherwise specified:

The term "biomolecule" refers to any biologically-derived or useful molecule such as peptides, proteins, carbohydrates, cytokines, growth factors, hormones, enzymes, toxins, anti-sense RNA, drugs, oligonucleotides, lipids, DNA, antigens, immunogens, and allergens.

The term "immunogen" refers to any substance, such as a molecule, cell, virus or fragment of such molecule, cell or virus which can be administered to an individual in an effort to elicit an immune response. The term "immunogen" thus simply refers to such substances which are or can be administered or otherwise used to raise antibodies or cellular immune system components, such as by "priming".

When used in connection with "immunogen", the term "molecule" refers to a molecule or molecular fragment of the antigen unless otherwise specified.

Likewise when used to refer to a cell, virus or fragment thereof, the immunogen can be the cell, virus or component thereof, which can be disposed in a complex in accordance with the present invention to enhance the immune response thereto. The term "immunogen" therefore encompasses antigenic compounds, such as foreign proteins as well as species which are essentially non-antigenic in the absence of the treatment described herein, cells, viruses, and cellular and viral components.

The term "antigen," which may be abbreviated "Ag," refers to substances, e.g., molecules which induce an immune response. It thus can refer to any molecule contacted by the immune system, and may include without limitation, proteins, nucleic acids and the like, and may even extend to carbohydrates capable of presentation in accordance herewith. Generally, each antigen typically comprises one or more epitopes. The terms antigen and immunogen are sometimes used interchangeably.

Certain antigens described herein or epitopes thereon in some instances may be considered poor antigens and may not substantially induce an immune response or other immunological reaction upon injection or other exposure to a normal, substantially immunocompetent host. They may also include scarce antigens that are difficult to obtain or purify, or antigens that require adjuvant or administration in large amounts for efficient immune responses. Based on the foregoing, "antigenicity" and "immunogenicity" are used interchangeably.

The term "protein" refers to synthetically produced and naturally occurring polypeptides, fragments of polypeptides and derivatives thereof which may provoke an immune response, either in vitro or in vivo. For convenience, but not by way of limitation, the description below utilizes the term "protein" but these teachings also apply to other compounds which either contain protein residues or that are otherwise structurally similar. Oligonucleotides, carbohydrates, and amine-containing lipids, as well as other reactive biomolecules may be mentioned as non-limiting examples. The teachings contained herein are therefore not to be limited to proteins or fragments thereof.

The terms "immunocompetent," "normal immune system" and like terms refer to the immune response which can be elicited in a normal mammalian host with the antigen of interest, when the antigen in question is administered without the modifications and preparation described herein. The immunogen can simply be administered to the host in unmodified form, and the normal immune response evaluated. Thus, using art recognized methods, this control is readily ascertained without resort to undue experimentation.

The term "antibody" refers to immunoglobulins, including whole antibodies as well as fragments thereof, such as Fab, F(ab')$_2$ or dAb, that recognize or bind to specific epitopes. The term thus encompasses, inter alia, polyclonal, monoclonal and chimeric antibodies, the last mentioned being described in detail in U.S. Pat. Nos. 4,816,397 and 4,816,567, which are incorporated herein by reference. An antibody "preparation" thus contains such antibodies or fragments thereof, which are reactive with an antigen when at least a portion of the individual immunoglobulin molecules in the preparation recognize (i.e., bind to) the antigen. An antibody preparation is therefore termed "non-reactive" with the antigen when the binding of the individual immunoglobulin molecules to the antigen is not detectable by commonly used methods.

An antibody is said to "recognize" an epitope if it binds to the epitope. Hence, "recognition" involves the antibody binding reaction with an epitope, which may include the typical binding mechanisms and methods. "Binding" is thus used in the conventional sense, and does not require the formation of chemical bonds.

The term "epitope" is used to identify one or more portions of an antigen or an immunogen which is recognized or recognizable by antibodies or other immune system components. The "epitope region," as used herein, refers to the epitope and the surrounding area in the vicinity of the epitope, taking into account three dimensional space. Hence, this may take into account the tertiary and quaternary structure of the antigen.

"Processing" and "presentation" refer to the mechanisms by which the antigen is taken up, altered and made available to the immune system. Presentation also includes, when appropriate, complexation or binding with MHC (see below) and other molecular events associated with generating an effective T-cell response. In certain instances, processing entails the uptake and partial proteolytic degradation of the antigen by APCs, as well as display on the APC surface in the context of MHC. The terms "reaction" and "complex" as well as derivatives thereof, when used in this general sense, and are not to be construed as requiring any particular reaction mechanism or sequence.

The abbreviation "MHC" refers to major histocompatibility complex, a series of compounds which is normally present to a greater or lesser degree on the surface of, among others, antigen presenting cells. MHC functions to "signal" cellular immune system components, e.g., T-lymphocytes, to recognize and react with the antigen presenting cell and/or the antigen bound to said cell and/or the MHCs thereof. The term "signal" is used in the general sense to refer to the initiation of the reaction between T-cells and APCs bearing processed antigen in the context of MHC. As such the "signal" may involve any reaction between these components which causes the antigen to become recognized by antibodies, an antibody preparation or by the cellular immune system components.

For purposes of the present invention, the term "$\alpha_2$-macroglobulin" and its abbreviation "a$_2$M" are to be used interchangeably. Moreover, the use of $\alpha_2$-macroglobulin in accordance with the present invention is believed to be more generally applicable to $\alpha$-macroglobulins and to the macroglobulin family, and the scope of the invention is to be interpreted in this broader fashion.

Preferably, the term $\alpha_2$M refers to human $\alpha_2$M. However, this term includes, but is by no means limited to, mouse $\alpha_2$M(a homotetramer), mouse $\alpha_1$-inhibitor-3 (a monomer); rat $\alpha_2$M (a homotetramer); rat $\alpha_1$M(a homotetramer); rat $\alpha_1$-inhibitor-3 (a monomer); rabbit $\alpha_1$M(a homotetramer); human pregnancy zone protein (a homodimer); cow $\alpha_2$M(a homotetramer); dog $\alpha_2$M(a homotetramer); duck ovostatin or ovomacroglobulin (a homotetramer); hen ovostatin or ovomacroglobulin (a homotetramer); frog $\alpha_2$M(a homotetramer); as well as receptor-binding fragments thereof.

The term "receptor-binding" refers to the ability to bind to a specific receptor on an APC. The receptor may mediate endocytosis, signaling and cell activation, or both. It is presently believed that there are two receptors for $\alpha_2$M. One receptor mediates signaling, and thus cellular activation and growth. The other receptor mediates endocytosis. A C-terminal fragment of $\alpha_2$M induces macrophage activation. When this fragment lacks a cis-dichlorodiamine platinum (cis-DDP)/oxidation sensitive reaction site, it appears to bind to the signaling receptor but not as well as the endocytic receptor. When the C-terminal fragment includes the cis-DDP/oxidation sensitive reaction site, it appears to bind to both receptors.

In accordance with the present invention, a structurally-defined and stable complex comprising an antigen and $\alpha_2$-macroglobulin is described which has utility in the modulation of the immune response. The present invention offers a facile and reproducible method for the preparation of a complex between a structurally-defined antigen and $\alpha_2$-macroglobulin, without limitation on the size of the antigen.

As described in the Background section, above, prior studies on the formation of a complex between an antigen, such as a protein, and $\alpha_2$-macroglobulin, demonstrated the requirement for proteolytic attack of the native $\alpha_2$-macroglobulin molecule to produce both a receptor-recognized form of the molecule as well as enable access of go the antigen to the $\alpha_2$-macroglobulin thiol ester, comprising a glutamyl residue at position 952 (Gln$^{952}$) and a cysteinyl residue at position 949 (Cys$^{949}$). The cleavage e of the thiol ester, formed from the respective amino acid residue amino and sulfhydryl group, provides potential covalent attachment sites for antigens. A nucleophilic amino acid residue on the antigen such as a lysine, when allowed to gain access to the thiol ester as a result of proteolytic cleavage, opens the thiol ester and becomes bound to the γ-glutamyl residue. The same antigen or a second antigen may also be bound to the cysteine residue by means of a disulfide bond. The antigen-$\alpha_2$-macroglobulin complex then, through processing by the immune system described in the Background section above, gives rise to an immune response to the antigen.

Previous studies on the thiol ester and antigen coupling to $\alpha_2$-macroglobulin led prior investigators to use small nucleophilic compounds (most often methylamine) to study the activation of $\alpha_2$-macroglobulin. In the absence of proteinases, these nucleophiles cleave the thiol ester and activate $\alpha_2$-macroglobulin, which has an intact bait region, to the receptor-recognized form. However, after addition of the nucleophile to the thiol ester, no further addition or substitution of another nucleophile, such as the lysyl residue of an antigen, was known or considered to occur.

The present inventors in studying the thiol ester and the reactivity of $\alpha_2$-macroglobulin to antigens made the surprising and remarkable discovery that a nucleophile-activated $\alpha_2$-macroglobulin could in fact undergo a nucleophilic exchange reaction with a protein or other antigen, under certain conditions. Conditions which permitted the nucleophilic exchange reaction were found to be incubation at an elevated temperature for an appropriate duration of time. For example, a protein antigen which is stable at elevated temperatures undergoes an exchange upon incubation of 1–5 hours at about 50° C. with nucleophile-activated $\alpha_2$-macroglobulin, which results in significant incorporation of the protein antigen into the $\alpha_2$-macroglobulin. Lower temperatures, such as at about 37° C., may achieve the nucleophilic exchange over a longer period of time, around 24 hours. The ability to covalently attach an antigen to $\alpha_2$-macroglobulin in the absence of proteinase offers a significant improvement over the prior art in the facile and reproducible preparation of structurally defined antigen-$\alpha_2$-macroglobulin conjugates for modulation of the immune response. One major advantage to this discovery is that antigens that had been unsuitable for coupling to $\alpha_2$-macroglobulin because of size and/or susceptibility to proteolytic attack may be coupled to nucleophile-activated $\alpha_2$-macroglobulin in the absence of proteinases by the methods of the present invention. Because the conditions under which conjugation of the antigen to $\alpha_2$-macroglobulin are defined, greater ratios of antigen to $\alpha_2$-macroglobulin may be achieved. Furthermore, when proteinases are used, incorporation of the proteinase into the $\alpha_2$-macroglobulin occurs, reducing the capacity of $\alpha_2$-macroglobulin for antigen and producing a complex with more than one antigen: the desired antigen and the undesired proteinase. Furthermore, if proteinase is used, antibodies could be raised against the proteinase itself. These undesirable conditions are obviated by the present invention. Taking advantage of the propensity for $\alpha_2$-macroglobulin to participate in the processing of antigens in the enhancement or suppression of the immune response, the ability to prepare a structurally-defined complex offers a greater ease in the preparation of vaccines.

The $\alpha_2$-macroglobulin useful in the present invention can be native or produced recombinantly, using well known techniques in molecular biology. The recombinant whole protein can be expressed in a glycosylated form, e.g., by expression in a yeast, baculovirus, or mammalian expression system; or in a non-glycosylated form, e.g., by expression in a bacterial expression system. In another embodiment, $\alpha_2$-macroglobulin can be prepared transgenically, for example, by expression in the milk of a transgenic animal, such as a cow, goat or sheep. In a preferred aspect, expression is carried out in a baculovirus expression system, which can provide for high yield, while avoiding the problem of endotoxin contamination that accompanies expression in bacterial systems, such as E. coli. Transgenic expression in milk as described above also avoids these problems.

Activation of $\alpha_2$M to form $\alpha_2$M* may be achieved with a suitable amine, such as that depicted by the formula $RNH_2$ wherein R is hydrogen or a straight-chain or branched lower alkyl group of from 1 to about 6 carbons, such as methyl, ethyl, n-propyl, isopropyl, n-butyl, isobutyl, t-butyl, and the like. Ammonia and methylamine are preferred.

As described above, it is a further advantage of the present invention that the size of the antigen to be coupled to $\alpha_2$-macroglobulin is not limited. Previous methods which use proteinases to activate $\alpha_2$-macroglobulin restrict the size of the coupled antigen to about 40 kilodaltons, corresponding to the 5 nm binding pocket formed in $\alpha_2$-macroglobulin after proteolytic cleavage. The methods of the present invention obviate the need for activation of $\alpha_2$-macroglobulin by a proteinase, and the size of the antigen desired to be incorporated is not limited, and may range in size, for example, from about 0.5 to 100 kilodaltons. The incorporation of the antigen or biomolecule into one or more of the thiol esters on a molecule of $\alpha_2$-macroglobulin may occur at the glutamyl, cysteinyl, or both residues formed from the cleavage of the thiol ester. A theoretical maximum of eight molecules of intact antigen per tetramer of $\alpha_2$-macroglobulin is possible.

It has also been found that the degree of antigen incorporation into $\alpha_2$-macroglobulin by the methods of the present invention may be increased. In previous methods using proteinase activation, a certain amount of the proteinase may be incorporated into the $\alpha_2$-macroglobulin, limiting the amount of antigen that may become coupled. Additionally, it has been found by the present inventors that mild oxidation of the antigen may be used to further increase the amount of antigen which may be incorporated into $\alpha_2$-macroglobulin. This may be achieved by the incubation of the antigen with an oxidizing agent such as N-chlorobenzenesulfonamide or other reagents which do not interfere with the structural or immunogenic properties of the antigen.

In a specific but non-limiting example of the practice of the present invention, $\alpha_2$-macroglobulin is activated to its receptor-recognized form by incubation with 200 mM ammonium bicarbonate, pH 8.5, for 1 hour. This treatment leads to the cleavage of the four thiol esters of the $\alpha_2$-macroglobulin. Subsequently, after removal of excess ammonium bicarbonate, the thiol-ester-cleaved $\alpha_2$-macroglobulin is incubated in 40-fold molar excess of an antigen such as lysozyme, streptokinase, or insulin. Incubation at 37° C. provides optimal incorporation of antigen after 24 hours; at 50° C., the reaction is faster and optimal incorporation occurs after 5 hours. The combination of temperature and time may be selected based on the temperature sensitivity and stability of the protein and the desired degree of coupling of the antigen to $\alpha_2$-macroglobulin; the skilled artisan will determine based on the characteristics of the particular antigen the optimal conditions for achieving the desired product. The Examples below provide specific but non-limiting conditions.

Numerous utilities of the antigen-$\alpha_2$-macroglobulin complexes of the present invention are contemplated. As will be illustrated by the following examples, these uses benefit from the ease and reproducibility of preparation, the absence of proteolytic cleavage, and the structural definition and stability of the complex prepared by the methods of the present invention. These examples are merely illustrative of the numerous utilities of the complex of the present invention and are not meant to be limiting. Other examples of utilities of the antigen-$\alpha_2$-macroglobulin complexes of the present invention may be found in PCT/US93/12479 to Duke University, incorporated herein by reference As indicated earlier, the utility of antigen-$\alpha_2$-macroglobulin complexes of the present invention is predicated on improved antigen presentation in vitro and more importantly, a dramatic increase in immune activity as measured by the development of antibodies to the antigen stimulus in vivo when antigen is coupled to $\alpha_2$-macroglobulin. This significant increase in activity is one aspect of the invention the other being the ability of the complex of the present invention to be prepared without use or inclusion of a proteinase. The ability to delete adjuvant from the formulations prepared in the present invention represents a further efficiency and likewise eliminates the potential for deleterious reactions and delays in uptake that have been experienced with adjuvant-containing formulations.

The present invention further extends to the preparation of antibodies to antigens, including where desired, the preparation of monoclonal and chimeric antibodies based upon those raised against the complexes of the present invention, as well as "primed" lymphocytes specific for the antigens. Likewise, the present invention can be used as a means for stimulating antigenicity and immunocompetence in instances where the particular antigen has previously failed to elicit immunologically or therapeutically significant arousal and activity in the host.

The utilities of the complexes of the present invention are primarily directed to the administration of antigens recognized by the macrophage in view of the existence on the macrophage of receptors for $\alpha_2$-macroglobulin. However, other APCs may possess receptors for $\alpha_2M$ and the present invention is accordingly intended to extend to the presentation of antigen to these other APCs.

By coupling the antigen with $\alpha_2$-macroglobulin in accordance with the present invention to form the complex of the invention and using the complex as the immunogen, a "modified immune response" can be achieved. This means that, e.g., the immunogen can be used to raise antibodies which are specific to epitopes either weakly or not previously recognized. Additionally, the modified immune response may involve non-antibody immune system components, e.g., T-lymphocytes, which may recognize an epitope not previously presented or recognized. Hence, the "modified immune response" is largely directed to the previously weakly or unrecognized epitope on the antigen treated, or epitopes requiring adjuvant or use of large amounts of antigen, all as described herein.

Additional preferred embodiments of the invention utilize the complex as the immunogen, and seek to raise or react said complex with antibodies which also recognize the same or a different epitope which is present on the molecule. In this aspect of the invention, the so-called modified immune response therefore involves the generation of antibodies which are not otherwise efficiently formed or observed in vitro or in vivo. It may also involve generation of antibodies or stimulation of lymphocytes that would not otherwise occur in the absence of noxious adjuvants not approved for human usage. Preferably, and advantageously, such antibodies can be generated by immunization in the absence of adjuvant. For example, the immunogen can be used to inoculate a mammal to raise antibodies to the newly recognizable epitope, and to produce antiserum or vaccine preparations, and the like.

Likewise, antibody molecules can be cleaved to form antibody fragments, which can be recombined in vitro to form chimeric antibodies which recognize or bind to newly recognizable epitopes on the antigen. Hence, the "modified immune response" is not limited to a conventional immune response, or to increases or decreases in the extent or severity thereof.

As stated earlier, both positive and negative regulation of the antigenicity of epitopes can be achieved. For example, by rendering epitopes recognized, or recognizable, antibodies can be raised to recognize and bind to the antigen. Enhanced antigenicity and the ability to raise antibodies to otherwise weak, scarce or ineffective epitopes finds great utility not only, for example, in vaccine applications in animals, including humans, but also in producing antibodies which can be used as reagents for, among other uses, binding, identifying, characterizing and precipitating epitopes and antigens, such as the production of antibodies against scarce antigens for research purposes.

Also, immunodominance of particular epitopes on a molecule may be modified. Certain antigens containing more than one epitope have characteristic immune responses based upon the dominance of one epitope over the other(s). This aspect of the invention enhances the recognition of the subordinate epitope(s) by either preparing and administering a complex of the invention to potentiate the recognition and activation of the subordinate epitope(s), or by preparing and administering a complex bearing an agent that will be recognized by the dominant epitope and suppress the recognition of the same by antigen.

A further embodiment may for example, take advantage of APC receptor proteins which recognize and bind to polypeptide molecules present on the antigen or in the complex of the invention.

Antigen uptake by the APCs can occur via nonspecific mechanisms, and may be followed by display of the antigen in association with MHC on the cell surface.

Once antigen is internalized by APCs, partial proteolytic degradation occurs in a prelysozomal endosome, and processed peptide fragments of the antigen become associated with MHC molecules. However, while partial proteolytic degradation of antigen may be essential in order to generate appropriate MHC and T-cell binding to the peptide fragments thereof, excessive degradation of antigen has been found to be detrimental to the eventual immune response. Inhibition of proteolysis which is not essential for the processing of a specific antigen has been shown to enhance processing and presentation, suggesting that the interference with inappropriate proteolysis actually enhances antigen presentation. The present invention provides methods for the preparation of the antigen-$\alpha_2$-macroglobulin complex comprising a structurally defined antigen for delivery to the APC and subsequent processing. Proteolytic degradation of the antigen during preparation of the complex is not desirable in order to achieve the desired immune response.

The antibodies described herein are typically those which recognize the epitopes on the antigens which are made recognizable, enhanced or suppressed as described above. By injecting this type of antigen into a mammal, such as through a hyperimmunization protocol, modulated antibody responses or CTL responses to the epitopes can be achieved.

The antibodies which are disclosed herein may be polyclonal, monoclonal or chimeric antibodies, and may be raised to recognize the desired epitope and used in a variety of diagnostic, therapeutic and research applications. For example, the antibodies can be used to screen expression libraries to ultimately obtain the gene that encodes proteins bearing the epitope evaluated. Further, antibodies that recognize the antigen presented can be employed or measured in intact animals to better elucidate the biological role that the protein plays, or to assess the state of immune response or immunologic memory more effectively.

Polyclonal, monoclonal and chimeric antibodies to the antigen can be prepared by well known techniques after immunization with a complex according to the invention, such as the hyperimmunization protocol, or the hybridoma technique, utilizing, for example, fused mouse spleen lymphocytes and myeloma cells. Immortal, antibody-producing cell lines can also be created by techniques other than fusion, such as direct transformation of lymphocytes with oncogenic DNA, or transfection with Epstein-Barr virus. Likewise, chimeric antibody molecules can be produced using an appropriate transfection and hybridoma protocol. In an analogous fashion, immortalized epitope-specific T-lymphocyte lines can also be developed.

The present invention also includes the immunogens which are produced and used as described herein in form. Thus, the preferred immunogen is an antigen prepared in a complex of the invention, which has at least one epitope. The immunogen has modified antigenicity due to the presence of, reaction with or linkage to the $\alpha_2$-macroglobulin molecule. The immunogen induces the formation or proliferation of T-cells of antibodies which recognize the protein in its modified form or in its non-modified form.

In a preferred embodiment, the antigen used in an immunogenic complex of the invention is a synthetic HIV peptide, e.g., as described in (52). Such synthetic peptides combine neutralizing B-cell sites from the third variable region (V3) of the HIV envelope peptide gp120, with the gp120 T-helper epitope T-1. Several of these synthetic peptides, designated T1-SP10, have been demonstrated to elicit high-titered neutralizing antibodies and T-cell responses in mice, goats, and rhesus monkeys, when administered in incomplete Freund's adjuvant (see Hart et al., supra). For example, the peptide T1-SP10MN(A) (MW 4771), which has the following amino acid sequence:

KQIINMWQEVGKAMYACTRPNYNKRKRIH
IGPGRAFYTTK (SEQ ID NO:1), can be complexed with $\alpha_2$M by incubation of the peptide with nucleophile-activated $\alpha_2$-macroglobulin in accordance with the methods of the present invention.

Other non-limiting examples of antigens which can be used in the immunogenic complexes of the present invention include another HIV-encoded hybrid peptide [T1-SP10IIB (A); sequence= KQIINMWQEVGKAMYACTRPNNNTRK-SIRIQRGPGRAFVTI (SEQ ID NO:2); ref. 52] encoding a HIV (human immunodeficiency virus) gp120 T-cell epitope (T1) (76); HBsAg, the protein representing one of the major surface antigens of human Hepatitis B Virus; peptide OS (amino acids 124–147 of HBsAg; sequence= CTTPAQGNSMFPSCCCTKPTDGNC, SEQ ID NO:3)(80); and a chimeric peptide (sequence= TRILTIPQSLDSCTKPTDGNC)(81) representing a T-cell epitope (amino acids 23–34) of HBsAg joined to the $NH_2$-terminus of a B-cell epitope (amino acids 139–147) of HbsAg. These examples are meant to be illustrative of the types and varieties of antigens that are suitable for preparing useful ininunogens of the present invention, and are not to be construed as limiting in any way as to the selection of antigen.

In another embodiment, an immune response to a particular antigen may be induced in an animal by exposing in vitro antigen presenting cells isolated from the animal to a complex of the antigen and $\alpha_2$M as described herein. After exposure, the antigen presenting cells may be reintroduced into the animal, and the thus-primed antigen presenting cells will induce an immune response to the antigen. For example, to induce an immune response to a tumor growing in a patient, a complex may be prepared between isolated cancer cell antigens and $\alpha_2$M. Dendritic cells may be isolated from a whole blood sample from the patient, and exposed to the tumor antigen-$\alpha_2$M complex in vitro. The dendritic cells are then reintroduced into the patient. A resulting immune response directed against the tumor antigen is thus elicited to attack the tumor.

Therapeutic treatments and diagnostic methods can be performed using any or all of the various components and processes described herein. For example, for the diagnosis or treatment of cancer or infection, an isolated protein can be derived from the tumor, abnormal cells or infectious organism, and this protein can be used as an antigen and prepared in a $\alpha_2$-macroglobulin complex following the method of the present invention. Antibodies to this protein can be elicited using the methods for enhanced antigen presentation disclosed herein and used to identify, characterize, bind, inhibit or inactivate, as desired, previously unknown or ineffective epitopes on the tumor, abnormal cell, bacterial or viral protein. This information, in turn, is useful for developing drugs which combat such afflictions, such as agonists, antagonists and the like.

Likewise, the antibodies described above can be raised to have direct diagnostic or therapeutic utility, particularly in oncologic, autoimmune and infectious disease treatments.

A preferred use for the antigen-$\alpha_2$-macroglobulin complex described herein is in the form of a vaccine which can be used to immunize mammalian patients in need of such treatment. By administering to such patient an effective amount of the immunogen, antibodies can be raised to the particular immunogen and immunogen-specific lymphocytes can be primed and activated, which are effective for treating disease or preventing the development or spread thereof. In a specific embodiment, the invention provides a vaccine against HIV.

The preferred non-cellular components which recognize antigen and which are used to characterize epitopes presented in accordance with the invention include the antibodies raised to an antigen which are not normally elicited in the absence of the methods described herein. Also, as noted above, the most preferred antibodies are raised to antigen in the complex, but recognize the non-modified molecule.

The general procedures set forth above are illustrated in the following non-limiting examples.

MATERIALS AND METHODS

Buffers, 5,5'-dithiobis(2-nitrobenzoate) (DTNB), hide powder azure, $NH_4HCO_3$, β-aminopropionitrile, iodoacetamide, porcine pancreatic elastase and bovine insulin were from Sigma (St. Louis, Mo.). Thiocyanic acid 2,4-dinitrophenyl ester (DNPSCN) was obtained from TCI America (Portland, Oreg.). Bovine serum albumin, RPMI medium and Earle's balanced salt solution were from Gibco BRL (Grand Island, N.Y.). Hen egg lysozyme was from Boehringer Mannheim. T1-SP10OMN(A) peptide was a kind gift from Dr. Barton F. Haynes, Duke University. IODO-BEADS were from Pierce (Rockford, Ill.) and New England Nuclear (Boston, Mass.) was the source of $^{125}$I-Bolton-Hunter reagent and Na$^{125}$I. The electrophoresis reagents were from Bio-Rad Laboratories (Richmond, Calif.) and frozen, platelet depleted, out-dated human plasma was from the American Red Cross (Charlotte, N.C.). C57BL/6 mice were obtained from Charles River Laboratories (Raleigh, N.C.). The spectrophotometers used were either a Shimadzu UV 160U (Columbia, Md.) or a Beckman DU®640 spectrophotometer (Arlington Heights, Ill.). The labeled proteins were counted in an LKB-Wallac 1272 CLINIGAMMA counter (Piscataway, N.J.) and gels with labeled proteins were analyzed in a PHOSPHORIMAGER™ 410A from Molecular Dynamics (Sunnyvale, Calif.).

Human $\alpha_2$M was purified as previously described (53). The concentration of intact thiol ester was determined by titration with DTNB (53,54). The protein concentration was based on $A_{280nm}$(1%(1%/1 cm)=8.93, molecular mass 718 kDa (55). The DTNB titration confirmed that more than 95% of the thiol esters in the $\alpha_2$M preparations were intact.

Unless otherwise stated the thiol ester-cleaved derivative, designated $\alpha_2$M*, was prepared by incubating $\alpha_2$M (2 to 6 mg/ml) with 0.2 M $NH_4HCO_3$ (pH adjusted to 8.5 with $NH_4OH$) for 60 min at room temperature. By this treatment more than 95% of the thiol esters were cleaved as judged by thiol ester titration with DTNB (53,54), electrophoretic mobility and in the hide powder azure assay (53,56,57). Excess modifying reagent was removed by gel filtration on a PD-10 SEPHADEX G-25 column (Pharmacia, Piscataway, N.J.). The buffer was, unless otherwise stated, 50 mM Tris, 50 mM NaCl, pH 7.5.

Lysozyme was brought into solution in water and diluted into an appropriate buffer. Insulin was brought into solution at acidic pH and diluted into an appropriate buffer. The purity of insulin and lysozyme was assured by reducing and non-reducing SDS-PAGE. The insulin concentration was based on $\epsilon_{280nm}$=5220 M$^{-1}$cm$^{-1}$ (58), and A$_{280nm}$(1%/1 cm)=26.5 was used for lysozyme (59). Insulin or lysozyme were incorporated into $\alpha_2$M by incubating desalted $\alpha_2$M* with excess ligand at 37° C. or 50° C. for 5–24 h. In some cases the complexes were separated from free ligand by gel filtration on a SEPHACRYL S-300-HR column (Sigma, St. Louis, Mo.). The extinction coefficient used for the complexes was that of free $\alpha_2$M, which is a reasonable estimate well within the experimental error. Proteins were concentrated using AMICON cells or CENTRICON® concentrators from Amicon (Danvers, Mass.).

Lysozyme and insulin were labeled with $^{125}$I-Bolton-Hunter reagent, basically as described by Bolton and Hunter (60). In some cases lysozyme or insulin were radio-iodinated using IODO-BEADS® according to the manufacturers specifications. Radioactivity was measured using an LKB 1272 γ-radiation counter.

SDS PAGE was performed in 4–20% gradient gels (10 cm×10 cm×1.5 mm) using the glycine/2-amino-2-methyl-1,3-propanediol/HCl system described by Bury (61).

Non-denaturing pore-limit PAGE separates proteins according to their radius of gyration and was carried out as previously described (53). When $\alpha_2$M is treated with NH$_3$ the thiol ester is cleaved and the conformational changes associated can be monitored by non-denaturing pore-limit PAGE (61–63). The electrophoretic mobility of native $\alpha_2$M is traditionally referred to as "slow" and that of nucleophile-inactivated $\alpha_2$M* as "fast". In all studies presented here the electrophoretic mobility of $\alpha_2$M and its derivatives will be referred to relative to these two standards. The pore-limit gels described here were 4–15% gradient gels (10 cm×10 cm×1.5 mm). In some cases the gels were dried and scanned for radioactive markers in a PHOSPHORIMAGER™.

The binding studies were performed basically as described by Imber and Pizzo (64). Peritoneal macrophages were obtained from thioglycolate stimulated C57BL/6 mice as previously described (65); plated in 24-well plates (2×10$^5$ cells/well), and incubated at 37° C. in a humidified CO$_2$ incubator. After equilibration at 4° C. the monolayers of cells were rinsed with ice cold Earle's balanced salt solution, 0.2% bovine serum albumin. Increasing concentrations (0.23 nM–60 nM) of $^{125}$I-labeled $\alpha_2$M*, or $\alpha_2$M* with protein ligand incorporated by incubation for 5 h at 50° C., were added to each well and allowed to incubate with gentle agitation at 4° C. for 16 h. Non-specific binding was determined in parallel experiments in which binding of radio-ligand took place in the presence of 10- to 100-fold molar excess of unlabeled ligand. Radio-ligand solution was removed from the wells, which were rinsed with Earle's balanced salt solution, 0.2% bovine serum albumin. The cells were solubilized with 1.0 M NaOH, 0.1% SDS and counted in the γ-counter. Specific binding was calculated from total binding minus nonspecific binding and K$_d$ was determined for each ligand by direct fit to the one site binding equation, using the non-linear data program SIG-MAPLOT® (Jandel Scientific, San Raphael, Calif.).

EXAMPLE 1

Figure 1B:
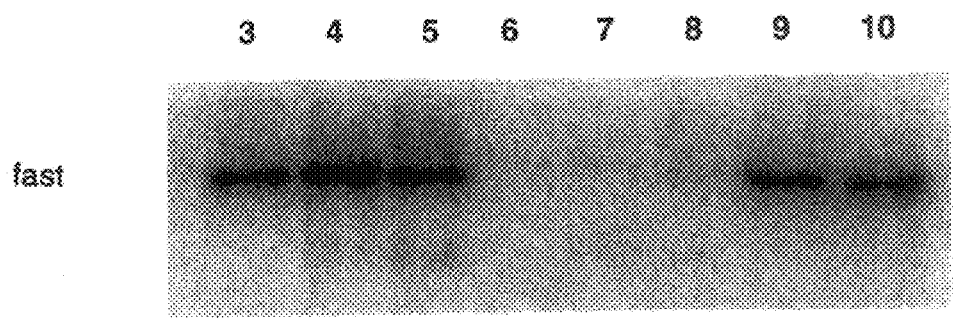
Figure 2A:
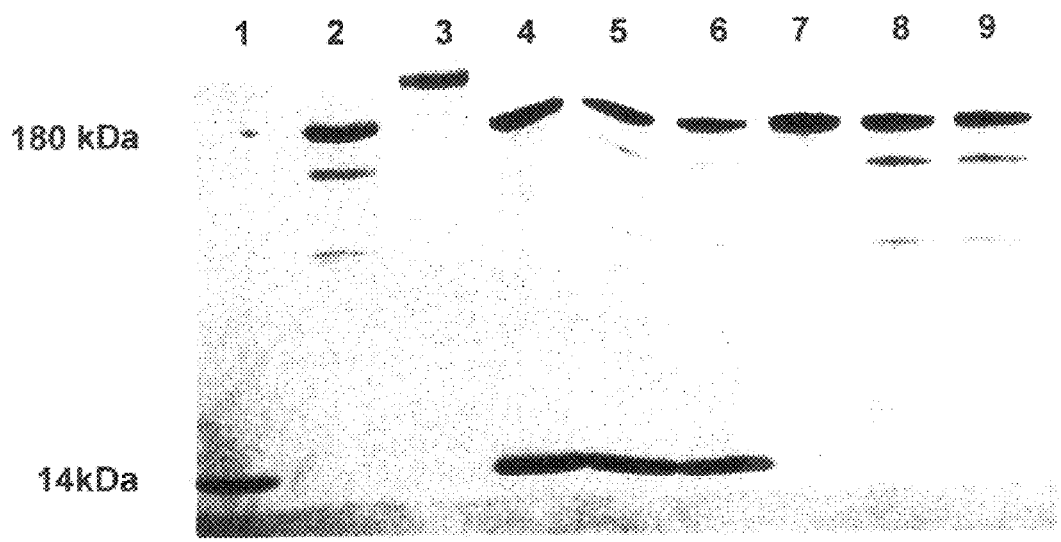
FIG. 2 depicts an electrophoretic analysis of a complex prepared at 50° C. by incubating Bolton-Hunter labeled lysozyme and $NH_3$-treated $\alpha_2$M*. At the indicated times, aliquots were frozen to be analyzed for electrophoretic mobility by 4–20% SDS PAGE (A) and PHOSPHORIMAGER™ scanning (B). After 5 h of incubation an aliquot was gel-filtrated, and the $\alpha_2$M-containing fractions pooled. The sample concentrations were not corrected for precipitation after prolonged exposure at 50° C. The lanes are as follows: 1, Bolton-Hunter labeled lysozyme; 2, reduced, isolated $\alpha_2$M*-lysozyme complex; 3, non-reduced, isolated $\alpha_2$M*lysozyme complex; 4–6, $\alpha_2$M* incubated with Bolton-Hunter labeled lysozyme at 50° C. for 0 h, 5 h and 24 h, respectively; 7–9, $\alpha_2$M* incubated at 50° C. for 0 h, 5 h and 24 h, respectively.
Figure 2B:
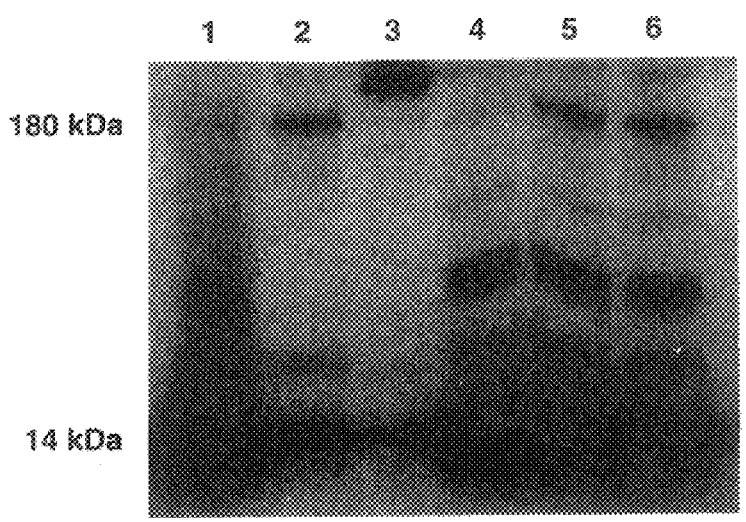

$\alpha_2$-Macroglobulin* was prepared as described above and incubated with a forty-fold molar excess of $^{125}$I-Bolton-Hunter-labeled hen egg lysozyme at 50° C. The samples were analyzed by non-denaturing pore-limit PAGE (FIG. 1A). The control samples, in the absence of lysozyme, behaved as expected (18), reverting to the "slow" migrating conformation characteristic of native $\alpha_2$M (FIG. 1A, lanes 6–8). However, in the presence of lysozyme there was a distribution of "slow" and "fast" migrating $\alpha_2$M even after 24 h at 50° C. (FIG. 1A, lane 5). The gels were dried and scanned for radioactivity on a PHOSPHORIMAGER (FIG. 1B). Radioactivity was identified only in the samples that had been incubated with $^{125}$I-lysozyme, and it migrated at the position corresponding to "fast", receptor-recognized $\alpha_2$M* (FIG. 1B, lanes 3–5). To further confirm the position of the radioactive band, an aliquot of the complex isolated after 5 h of incubation (see below) was incubated with an excess of porcine pancreatic elastase. Coomassie blue staining confirmed that all the protein shifted to migrate in the same position as the radioactive band, "fast" $\alpha_2$M* (FIG. 1, lanes 9 and 10). Studies were attempted utilizing increasing concentrations of lysozyme in an effort to prevent $\alpha_2$M* from reverting to the "slow" migrating conformation. However, due to solubility problems it was not possible to drive the reaction to completion, and in all experiments some $\alpha_2$M* reverted to the "slow" migrating native conformation with no lysozyme associated. SDS-PAGE analysis confirmed that not all the lysozyme associated with $\alpha_2$M* was covalently incorporated (FIG. 2). With the samples which were kept on ice or at room temperature most of the radioactivity was released from $\alpha_2$M* by heating the sample to 100° C. in the presence of 1% SDS (FIG. 2B, lane 4). Covalent incorporation of $^{125}$I-lysozyme into $\alpha_2$M* was observed only after prolonged incubation at 50° C. (FIG. 2B, lanes 5 and 6, radioactive band at the position of the 180 kDa subunit of $\alpha_2$M). A time course study determined optimal conditions for covalent ligand incorporation to be 5 h at 50° C.

EXAMPLE 2

To further characterize the complex, $\alpha_2$M* was incubated with a forty-fold excess of $^{125}$I-Bolton-Hunter labeled lysozyme at 50° C. (5 h) as described above. The complex formed was separated from the free ligand by gel filtration on an S-300-HR column. As expected, both "fast" and "slow" migrating $\alpha_2$M was present when analyzed by non-denaturing pore-limit PAGE (FIG. 1A, lane 9). It is not possible to separate the two forms of the macroglobulin by gel filtration and the stoichiometry presented is based on the mixture of the two forms. The amount of lysozyme incorporated was determined from the total protein concentration (A$_{280nm}$), the radioactivity incorporated, and the specific radioactivity of the $^{125}$I-Bolton-Hunter labeled lysozyme (3000–5000 c.p.m./pmol). The complex had approximately 2.3 moles of lysozyme bound to each mole of $\alpha_2$M (see Table 1 below). More than 94% of the radioactivity of the complex was precipitated with 25% trichloroacetic acid, indicating that it is all associated with protein. To characterize the stability of the complex, an aliquot was boiled for 30 min followed by centrifugal microfiltration in CENTRICON 100 microconcentrators (cut-off at 100 kDa), to isolate any free lysozyme or radioactive label. The filtrate was analyzed for radioactive counts and less than 15% of the radioactivity of the complex was released. The level of non-covalent binding was quantified by denaturing the complex in 1% SDS, 30 min at 100° C., followed by centrifugal microfiltration. Approximately 60% of the counts remained in the $\alpha_2M^*$-complex indicating that 1.4 moles of lysozyme bound covalently to one mole of $\alpha_2M^*$ at 50° C. (5 h). Analysis of the complex by SDS-PAGE confirmed the stoichiometry (FIG. 2, lanes 2 and 3). Before electrophoresis, the samples were boiled for ten min in the presence of 1% SDS, and, in some cases, 50 mM DTT. After drying, the gels were subjected to imaging on a PHOSPHORIMAGER. The radioactive bands were quantified either by the program provided with the PHOSPHORIMAGER or by excising bands from the gels and counting in a gamma-counter; both methods gave very similar results. Under non-reducing, denaturing conditions, approximately 1.6 moles of $^{125}$I-lysozyme remained bound per mole of complex (FIG. 2B, lane 3). When 50 mM DTT was present during the SDS treatment approximately 0.6 moles of $^{125}$I-lysozyme remained bound to $\alpha_2M$ per mole of complex (FIG. 2B, lane 2). The radioactivity migrated at positions corresponding to either the electrophoretic mobility of free lysozyme or the 180 kDa subunit of $\alpha_2M$.

TABLE 1

| Interaction | Moles of labeled ligand bound per mole of $\alpha_2M^*$ Ligand and Condition | |
|---|---|---|
| | Lysozyme 37° C. (24 h) | Lysozyme 50° C. (5 h) |
| Covalent and non-covalent | 6.6 | 2.3 |
| $Cys^{949}$ and $Gln^{952}$ mediated (SDS resistant) | 1.3 | 1.4 |
| $Gln^{952}$ mediated (SDS and DTT resistant) | 1.0 | 0.6 |

EXAMPLE 3

Figure 3A:
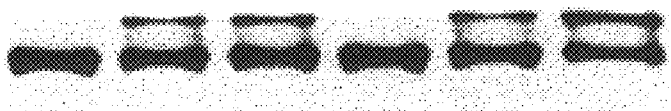
FIG. 3 depicts an electrophoretic analysis of a complex prepared at 37° C. by incubating Bolton-Hunter labeled lysozyme and $NH_3$-treated $\alpha_2$M*. At the indicated times, aliquots were frozen to be analyzed for electrophoretic mobility by non-denaturing 4–15% pore-limit PAGE (A) and PHOSPHORIMAGER™ scanning (B). The lanes are as follows: 1–3, $\alpha_2$M* incubated with $^{125}$I-Bolton-Hunter labeled lysozyme at 37° C. for 0 h, 5 h and 24 h, respectively; 4–6, $\alpha_2$M* alone incubated at 37° C. for 0 h, 5 h and 24 h, respectively.
Figure 3B:
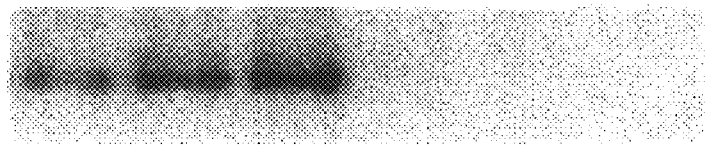

The efficiency of the reaction at lower temperatures was investigated. $\alpha_2M^*$ was incubated with a forty-fold excess of $^{125}$I-lysozyme at 23° C. and 37° C. and a time course study was performed. Even after 24 h of incubation at 23° C., there was no covalent incorporation of lysozyme into $\alpha_2M^*$, as analyzed by SDS-PAGE and centrifugal microfiltration of the SDS treated, isolated complex. As was observed at 50° C., at 37° C. the time-dependent electrophoretic mobility pattern of $\alpha_2M^*$ changed in the presence of lysozyme and less of the macroglobulin reverted to the "slow" migrating conformation characteristic of native a $\alpha_2M$ (FIG. 3A, lanes 3 and 6). SDS-PAGE determined the optimal time for covalent incorporation to 24 h. The complex which was isolated after 24 h at 37° C. had approximately 6.6 moles of lysozyme bound to each mole of $\alpha_2M$ (see Table 1 above). The level of non-covalent binding was quantified by denaturing the complex in 1% SDS, 30 min at 100° C., followed by centrifugal microfiltration. Approximately 1.3 moles of lysozyme remained covalently bound per mole of $\alpha_2M^*$-complex (Table 1, above). Analysis of the complex by SDS-PAGE confirmed the stoichiometry (FIGS. 4A and 4B). Under non-reducing conditions approximately 1.3 moles of lysozyme remained bound to each mole of $\alpha_2M$. When 50 mM DTT was present during the SDS treatment, 1.0 mole of $^{125}$I-lysozyme remained bound per mole of $\alpha_2M$. It appears that at 37° C. a higher fraction of the covalent binding is resistant to reduction than at 50° C.

EXAMPLE 4

The non-proteolytic, covalent incorporation of protein into $\alpha_2$-macroglobulin* is not limited to lysozyme. The smaller protein insulin behaved very similarly. $\alpha_2$-macroglobulin* was incubated with a forty-fold excess of $^{125}$I-Bolton-Hunter labeled insulin at 37° C. or 50° C. for 5 or 24 h. At each condition the complex formed was analyzed by non-denaturing pore-limit PAGE and both "fast" and "slow" migrating $\alpha_2$-macroglobulin was present, as described above. The amount of insulin covalently incorporated was determined by SDS-PAGE in a time course study. The optimal conditions for incorporation were (as for lysozyme) 5 h at 50° C. or 24 h at 37° C. The complex formed at 5 h incubation at 50∞C had 3 moles of insulin bound covalently to each mole of $\alpha$2-macroglobulin*. Under reducing conditions only 0.3 moles of insulin remained bound per mole of $\alpha$2-macroglobulin*. As was observed with lysozyme, the complex was more resistant to reduction when formed at 37° C. relative to 50° C. In the absence of reducing agents 2.5 moles of insulin bound covalently per mole of complex formed at 37° C. (24 h). Under reducing conditions approximately 1.6 moles of $^{125}$I-insulin remained bound to each mole of $\alpha$2-macroglobulin*. These data are summarized below:

TABLE 2

| Interaction | Moles of labeled ligand bound per mole of $\alpha_2M^*$ Ligand and Condition | |
|---|---|---|
| | Insulin 37° C. (24 h) | Insulin 50° C. (5 h) |
| $Cys^{949}$ and $Gln^{952}$ mediated (SDS resistant) | 2.5 | 3.0 |
| $Gln^{952}$ mediated (SDS and DTT resistant) | 1.6 | 0.3 |

EXAMPLE 5

The covalent bond between lysozyme and "fast" migrating $\alpha_2M^*$ in the complex was further characterized. Native, "slow" migrating $\alpha_2M$ was incubated with $^{125}$I-lysozyme at 37° C. (24 h) or 50° C. (5 h). The samples were analyzed by SDS-PAGE as described above (gels not shown). At 37° C. the covalent incorporation into native $\alpha_2M$ was less than 7% of the incorporation into the thiol ester cleaved, "fast" migrating $\alpha_2M^*$. At 50° C. the covalent incorporation into native $\alpha_2M$ was approximately 10% of the incorporation into $\alpha_2M^*$. The only chemical difference between native $\alpha_2M$ and thiol ester cleaved $\alpha_2M^*$ is the release of free Cys949 and the modification of Gln952 with $-NH_2$ in $\alpha_2M^*$. The limited incorporation of ligand into native $\alpha_2M$ indicates that the majority of the covalent incorporation of lysozyme into $\alpha_2M^*$ is mediated through the components of the thiol ester, either through nucleophilic exchange at $Gln^{952}$ or through thiol-disulfide exchange at $Cys^{949}$. This was further investigated by examining the incorporation of protein ligand in the presence of competing nucleophiles or thiol specific reagents. In some experiments, incubations of $\alpha_2M^*$ and $^{125}$I-lysozyme were carried out in the presence of 150 mM β-aminopropionitrile, a reagent that competes for incorporation into the glutamyl residue of the thiol ester (20). Some incubations were carried out in the presence of 0.65 mM DNPSCN or 0.1 mM iodoacetamide, reagents that modify $Cys^{949}$ in $\alpha_2M^*$ (66–71) (at higher concentrations of reagents the protein precipitated during incubation at elevated temperatures). In parallel experiments $\alpha_2M^*$ was incubated with either $^{125}$I-lysozyme or the modifying reagents alone. The samples were analyzed for radioactive protein incorporation in $\alpha_2M^*$ by SDS-PAGE.

| Amino acid residue targeted by competing reagent | Percent of labeled lysozyme bound to $\alpha_2 M^*$ in the presence of competing reagent, relative to conditions where no thiol ester specific reagents are present | |
|---|---|---|
| | 37° C., 24 h | 50° C., 5 h |
| $Gln^{952}$ | 40% | 40% |
| $Cys^{949}$ | 55% | 30% |

After 5 h at 50° C., the samples with β-aminopropionitrile present had incorporated approximately 40% of the lysozyme incorporated in the absence of β-aminopropionitrile. In the presence of DNPSCN or iodoacetamide, the incorporation represented close to 30%. After 24 h at 37° C., the samples with β-aminopropionitrile present had incorporated approximately 40% of the lysozyme incorporated in the absence of β-aminopropionitrile. In the presence of DNPSCN or iodoacetamide the incorporation was 50–60%. Thus, modification of either $Gln^{952}$ or $Cys^{949}$ in $\alpha_2 M^*$ reduces the incorporation of protein ligand significantly.

EXAMPLE 6

$\alpha_2 M^*$ and $\alpha_2 M^*$-lysozyme complex formed by incubation at 50° C. (5 h) were radio-iodinated with $Na^{125}I$ and the binding to macrophages was examined. The two samples bound to the macrophages with similar affinity; $K_d(\alpha_2 M^*)$= 5±2 nM and $K_d$(complex)=8±2 nM. In the complex sample, both "slow" migrating and receptor-recognized $\alpha_2 M^*$ are present. We did not separate the two forms of the macroglobulin and the stoichiometry is based on the mixture of the two forms, disregarding the fact that only the receptor-recognized form binds to macrophages. This may explain why the $K_d$ for the complex is slightly higher than for $\alpha_2 M^*$ itself. However, the observed values are within experimental error for such studies, and consistent with our $K_d$ value for binding of $\alpha_2 M^*$ to the LRP receptor (72).

EXAMPLE 7

Figure 5:
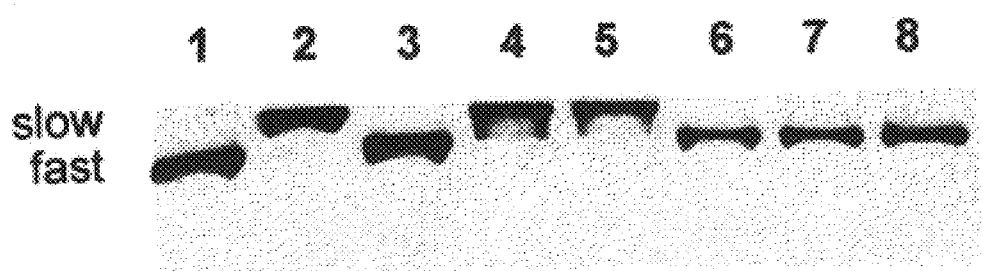
FIG. 5 depicts an electrophoretic analysis of $^{125}$I-radio-iodinated hen egg lysozyme in complex with $\alpha_2$M* by non-denaturing pore-limit PAGE. $\alpha_2$M* was prepared as described in Example 1 and incubated with buffer (lanes 3–5) or radio-iodinated lysozyme (lanes 6–8) at 50° C. At the indicated times aliquots were frozen to be analyzed for electrophoretic mobility by non-denaturing 4–15% pore-limit PAGE. The sample concentrations were not corrected for precipitation after prolonged incubation at 50° C. The lanes are as follows: 1, "fast" migrating $\alpha_2$M*; 2, "slow" migrating $\alpha_2$M; 3–5, $\alpha_2$M* incubated at 50° C. for 0 h, 5 h and 24 h, respectively; 6–8, $\alpha_2$M* incubated with radio-iodinated lysozyme at 50° C. for 0 h, 5 h and 24 h, respectively.

In one series of experiments hen egg lysozyme was radio-iodinated with $Na^{125}I$ by the method of chemical oxidation with N-chloro-benzenesulfonamide immobilized on polystyrene beads (IODOBEADS®). The reaction between the radio-iodinated lysozyme ($^{125}I$-lysozyme) and $\alpha_2 M^*$ appeared to be more effective than with $^{125}I$-Bolton-Hunter labeled hen egg lysozyme. $\alpha_2 M^*$ was incubated with a forty-fold excess of $^{125}I$-lysozyme at 50° C. In a parallel experiment $\alpha_2 M^*$ was incubated at 50° C. in the absence of lysozyme, and the samples were analyzed at 0 h, 5 h and 24 h by non-denaturing pore-limit PAGE. As described above, the control samples, with no lysozyme present, reverted almost fully to the "slow" migrating conformation characteristic of native $\alpha_2 M$ (FIG. 5, lanes 3–5). However, in the presence of $^{125}I$-lysozyme all the protein and radioactivity migrated as "fast", receptor-recognized $\alpha_2 M^*$, even after 24 h at 50° C. (FIG. 5, lanes 6–8). Free $^{125}I$-lysozyme was separated from the complex (after 5 h at 50° C.) by gel filtration on an S-300-HR column. The amount of lysozyme bound to $\alpha_2 M$ in the $\alpha_2 M^*$-$^{125}I$-lysozyme complex was determined from the radioactivity incorporated and the specific radioactivity of the lysozyme used for complex formation (18500 c.p.m./pmol). Approximately 2.7 moles of $^{125}I$-lysozyme were bound per mole of $\alpha_2 M^*$. The level of covalent binding was quantified by denaturing the $\alpha_2 M^*$-containing fractions in 1% SDS for 30 min at 100° C., followed by centrifugal microfiltration in CENTRICON® 100 microconcentrators, to isolate any free lysozyme. Approximately 75% of the counts remained in the $\alpha_2 M^*$-$^{125}I$-lysozyme complex indicating that 2 moles of hen egg lysozyme bind covalently to one mole of $\alpha_2 M^*$. When analyzed by non-denaturing pore-limit PAGE, the $\alpha_2 M^*$-$^{125}I$-lysozyme complex migrated exclusively as "fast", receptor-recognized $\alpha_2 M^*$ suggesting that the equilibrium has been driven towards complete complex formation.

The complex was further characterized by SDS PAGE (gels not shown). Before electrophoresis, the samples were boiled for ten min in the presence of 1% SDS, and, in some cases, 50 mM DTT, and the gels were analyzed on the PHOSPHORIMAGER™. Under non-reducing conditions SDS released approximately 0.3 moles of free $^{125}I$-lysozyme per mole of $\alpha_2 M^*$-$^{125}I$-lysozyme complex, whereas 1.6 moles of $^{125}I$-lysozyme remained bound per mole of complex. In the presence of both 50 mM DTT and 1% SDS, 0.8 moles of free $^{125}I$-lysozyme were released per mole of $\alpha_2 M^*$-$^{125}I$-lysozyme complex, whereas 1.2 moles of $^{125}I$-lysozyme remained in complex per mole of $\alpha_2 M^*$. It appears that the degree of covalent interaction obtained with radio-iodinated lysozyme is higher than that obtained with $^{125}I$-Bolton-Hunter labeled lysozyme and a higher fraction of the covalent binding is resistant to reduction. Since the Bolton-Hunter reagent reacts with lysyl residues it is possible that the lower degree of covalent incorporation observed with Bolton-Hunter labeled hen egg lysozyme is caused by the availability of fewer groups for nucleophilic exchange at the site of the thiol ester. However, $\alpha_2 M^*$ incubated with non-treated lysozyme at 50° C. had a migration profile in pore-limit PAGE identical to $\alpha_2 M^*$ incubated with $^{125}I$-Bolton-Hunter labeled lysozyme (gels not shown) and the distribution between "slow" and "fast" migrating $\alpha_2 M^*$-complexes was the same. When the experiments were repeated with lysozyme that was exposed to oxidation by IODOBEADS®, in the absence of $Na^{125}I$, native pore-limit PAGE confirmed that the reaction with $\alpha_2 M^*$ was complete, and all $\alpha_2 M^*$-complexes remained in the "fast" migrating conformation even after 24 h at 50° C. We therefore assume that the mild oxidation "primes" the amino acid residues of the ligand to react more readily with $\alpha_2 M^*$ and to exchange with -$NH_2$ at $Gln^{952}$ of the thiol ester in $\alpha_2 M^*$. This mechanism has not been previously described and we speculate that the enhanced reactivity is due to oxidation of amino acid side chains on lysozyme.

EXAMPLE 8

Figure 6:
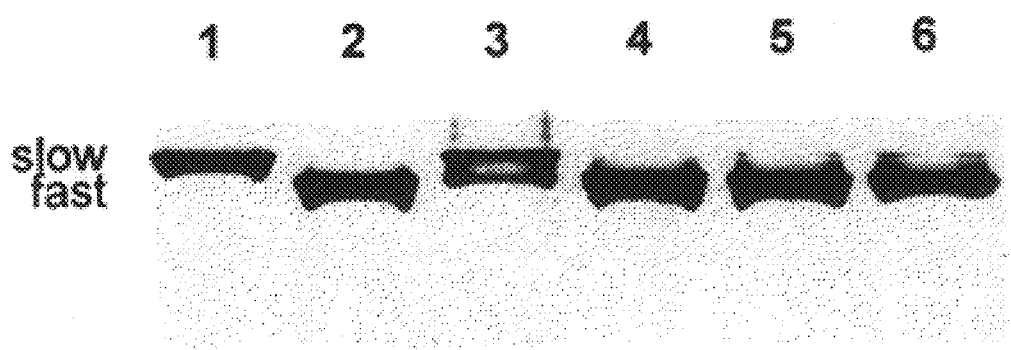
FIG. 6 depicts an electrophoretic analysis of the complex of $^{125}$I-radio-iodinated insulin and $\alpha_2$M* formed at 50° C., analyzed by non-denaturing pore-limit PAGE. $\alpha_2$M* was incubated with buffer (lanes 2–3) or 40-fold molar excess of radio-iodinated insulin (lanes 4–5) at 500. After 5 hours, an aliquot of the insulin containing mixture was gel-filtrated, and the $\alpha_2$M*-containing fractions pooled (lane 6). At the indicated times aliquots were placed on ice to be analyzed for electrophoretic mobility by non-denaturing 4–15% pore-limit PAGE. The lanes are as follows: 1, "slow" migrating $\alpha_2$M*; 2 and 3, $\alpha_2$M* incubated at 50° C. for 0 and 5 hours, respectively, with buffer; 4 and 5, with radio-iodinated insulin at 50° C. for 0 and 5 hours, respectively; 6, isolated $\alpha_2$M*-insulin complex.
Figure 7A:
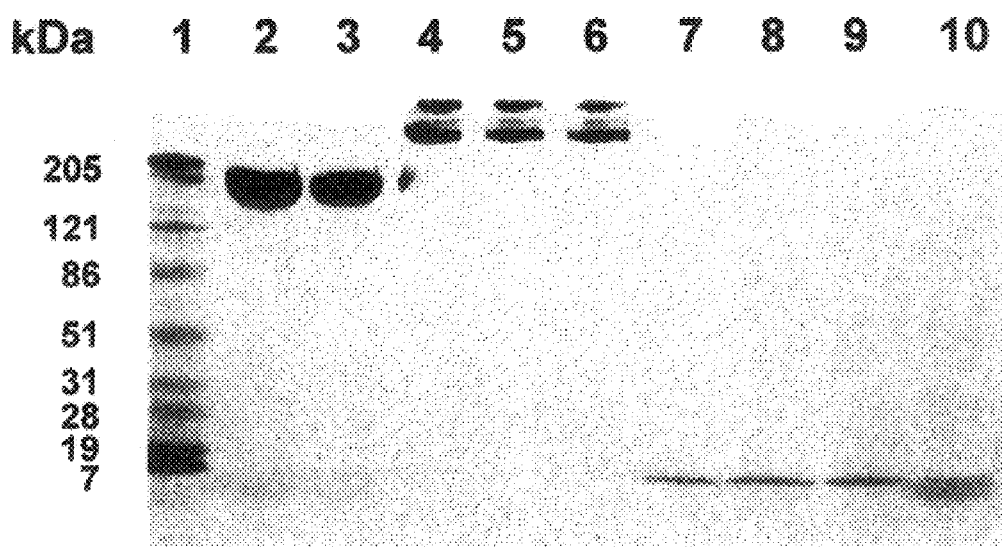
FIG. 7 depicts the denatured, electrophoretic analysis of $^{125}$I-radio-iodinated insulin in complex with $\alpha_2$M*. $\alpha_2$M* was incubated with 40-fold molar excess of radio-iodinated insulin at 50° C. After 5 h an aliquot was gel-filtrated, and characterized by SDS-PAGE (A) and PHOSPHORIM-AGER scanning (B). The lanes are as follows: 1, molecular weight markers; 2–3, reduced $\alpha_2$-macroglobulin*-insulin complex; 4–6, non-reduced $\alpha_2$-macroglobulin*-insulin complex; 7–9, non-reduced, radio-iodinated insulin; 10, reduced, radio-iodinated insulin.
Figure 7B:
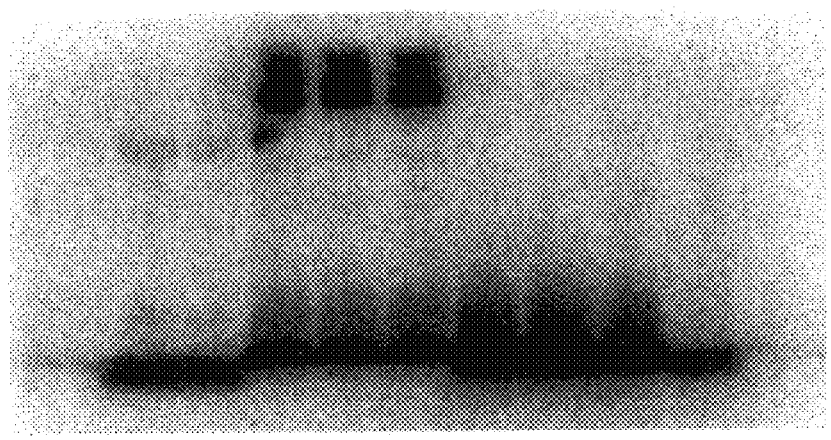

The above experiments were repeated using insulin. Interestingly, the smaller protein insulin behaved similarly to hen egg lysozyme. When insulin was radio-iodinated with $Na^{125}I$, by the method of chemical oxidation using IODOBEADS®, the ligand was fully incorporated into $\alpha_2 M^*$ after incubation for 5 h at 50° C. In non-denatured pore-limit PAGE all protein and radioactivity migrated as one band at the position corresponding to "fast", receptor-recognized $\alpha_2 M^*$ (FIG. 6, lanes 4–6). After isolation of the $\alpha_2 M^*$-insulin complex, 7.5 moles of $^{125}I$-insulin were found bound per mole of $\alpha_2 M^*$. Covalent binding accounted for approximately 57% of the insulin in the $\alpha_2 M^*$$^{125}I$-insulin complex (4.3 moles of insulin per mole of $\alpha_2 M^*$), as quantified by centrifugal microfiltration. The complex was analyzed by SDS PAGE (FIGS. 7A and 6B, lanes 2–6). Under non-reducing conditions SDS released 2.8 moles of free $^{125}I$-insulin per mole of $\alpha_2 M^*$-$^{125}I$-insulin complex, whereas 3.3 moles of $^{125}I$-insulin remained in complex with each mole of $\alpha_2 M^*$ (FIG. 7B, lanes 4–6). When 50 mM DTT was present during the SDS treatment 7 moles of $^{125}$I-insulin were released per mole of $\alpha_2$M and very little radioactivity remained associated with the macroglobulin (FIG. 6B, lanes 2 and 3). In parallel experiments $\alpha_2$M* was incubated at 50° C. in the presence of non-treated, native insulin and the samples were analyzed by non-denaturing pore-limit PAGE at 0 h, 5 h and 24 h. As described for lysozyme some of the $\alpha_2$M* reverted to a "slow" migrating conformation with no insulin incorporated and the reaction was not as complete as when insulin was primed by oxidation using IODO-BEADS®. The data presented in the above examples show that lysozyme and insulin can incorporate covalently into nucleophile-treated $\alpha_2$M* when co-incubated at 37° C. (24 h) or 50° C. (5 h). Approximately 6.6 (37° C.) or 2.3 (50° C.) moles of lysozyme bound per mole of $\alpha_2$M. Boiling of the $\alpha_2$M*-lysozyme complex released 15%–25% of the radioactivity incorporated. Boiling in the presence of 1% SDS released significantly more, indicating that at 50° C. (5 h) or 37° C. (24 h) approximately 1.4 moles of lysozyme incorporated covalently per one mole of $\alpha_2$M. This exceeds the values obtained by proteolytic incorporation where only one mole of lysozyme bound covalently per mole of $\alpha_2$M (27). During the proteolytic reaction, the proteinase is co-trapped with the ligand in the internal cavity of $\alpha_2$M and the size of the ligand and the proteinase limits the number of molecules that can be incorporated. Furthermore, the activating proteinase competes with lysozyme for reaction with the thiol esters. Interestingly, when incorporated through a proteolytic mediator the bond between lysozyme and $\alpha_2$M was resistant to reduction (27), whereas we find that some of the lysozyme incorporated by nucleophile activation is released from the $\alpha_2$M*-lysozyme complex by reduction. During the proteolytic activation, nucleophiles on the surface of the protein can react with the $\beta$-glutamyl group of the thiol ester (Gln$^{952}$), but in $\alpha_2$M*, this group is modified with —NH$_2$. The thiol group from the thiol ester (Cys$^{949}$) is, however, available for thiol-disulfide interchange (73). It appears that temperature affects the distribution between Gln$^{952}$ and Cys$^{949}$ incorporation. The complexes formed at 37° C. were more resistant to reduction than the complexes formed at 50° C. indicating a increase in preference for reaction with Cys$^{949}$ as opposed to exchange of nucleophiles at the site of Gln$^{952}$ at the elevated temperature.

Mild oxidation of lysozyme and insulin resulted in increased incorporation into $\alpha_2$M*. The improved incorporation induced by oxidation has not been previously described and we speculate that it is due to amino acid residues in the protein ligand undergoing oxidation to a more reactive nucleophilic state.

Insulin is a small, growth factor-like molecule of a size (6 kDa) at the limit of what can diffuse in and out of the closed trap in $\alpha_2$M* whereas lysozyme (14 kDa) is too large for diffusion (35). Incubation at 50° C. allows approximately 3 moles of insulin to covalently incorporate per mole of $\alpha_2$M*, which is comparable to the proteolytic incorporation of 3–4 moles of insulin per mole of $\alpha_2$M (21).

From a structural point of view, the ability of nucleophile inactivated $\alpha_2$M* to entrap and form SDS-stable complexes with diverse, non-proteolytic proteins, expands the previously characterized binding mechanisms known for $\alpha_2$M and $\alpha_2$M* (as reviewed in (74) and (75)).

EXAMPLE 9

In this example, the ability of complexes formed from streptokinase and amine-activated $\alpha_2$-macroglobulin to induce an immune response in human immune cells was evaluated. Streptokinase was purified from KABIKINASE (Pharmacia Adria) obtained from the Duke University Medical Center pharmacy according to the methods of Castellino et al. (Methods in Enzymology XLV:244–257). It was necessary to repurify the original material in order to obtain streptokinase free of human serum albumin which is used as a carrier in KABIKINASE. $\alpha_2$-Macroglobulin was purified from outdated human plasma (American Red Cross, Durham, N.C.) by the procedure described in (64). LAL endotoxin test kits were obtained from Associates of Cape Cod and endotoxin removal columns (Detoxi-Gel) from Pierce Chemical Company (Rockford, Ill.).

Normal peripheral blood mononuclear cells (PBMC) were obtained using sterile conditions from 10% citrated (acid citrate dextrose; Sigma; St. Louis, Mo.) venous blood obtained from healthy volunteers under informed consent. The blood was diluted 1:1 in a 50-mL conical polypropylene centrifuge tube with sterile phosphate-buffered saline (PBS; GIBCO BRL; Gaithersburg, Md.), underlaid with an equal volume of LSM (Lymphocyte Separation Media; Organon Teknika Corp.; Durham, N.C.), and the tubes centrifuged at 400×g and 20° C. for 40 min. The mononuclear cell band was removed to a fresh tube, the cells washed twice with PBS, and the cells resuspended at a concentration of 2×10$^6$/mL in Complete RPMI Media (RPMI 1640 supplemented with 25 mM HEPES, 5% heat-inactivated [56° C., 30 min] pooled human AB serum, 1% NUTRIDOMA HU [Boehringer Mannheim], 100 $\mu$M MEM non-essential amino acids, 2 mM L-glutamine, 100 U/mL penicillin, 100 $\mu$g/mL streptomycin, 1 mM sodium pyruvate).

$\alpha_2$-Macroglobulin (2.5 mL; 9.6 $\mu$M) was added to 408 $\mu$L of 1.5 M NH$_4$HCO$_3$, pH 8.0, and incubated for 60 min at room temperature. The $\alpha_2$-macroglobulin was then run over a PD-10 column (Pierce; Rockford, Ill.) equilibrated with PBS (10 mM Na$_2$HPO$_4$, 50 mM NaCl, pH 7.4) in order to effect a buffer exchange. The $\alpha_2$-macroglobulin, now in its so-called "fast form," is hereinafter designated $\alpha_2$-macroglobulin* and had an A$_{280}$=2.227 in a 1 cm cuvette. SK, previously purified from KABIKINASE, had an A$_{280}$=2.088, corresponding to a concentration of 46.4 $\mu$M. To prepare the $\alpha_2$-macroglobulin*/SK complexes, 6.0 mL of SK (ca. 280 nmol) was mixed with 2.0 mL of $\alpha_2$M* (ca. 7 nmol), sterile-filtered through a 0.45$\mu$ low-protein binding filter, and incubated for 24 hr at 37° C. The mixture was then loaded onto a SEPHACRYL S-300-HR column (1.5×96 cm; 170 mL bed volume; Pharmacia) equilibrated with PBS in order to separate complexes from free SK. The column was run at a flow of 40 mL/hr and fractions collected every 6 minutes. Fractions were analyzed by SDS-PAGE using 5–15% gradient gels under reducing conditions. The fractions (#21–23) representing the majority of the peak (determined by A$_{280}$ readings of each fraction) corresponding to the $\alpha_2$M*/SK complexes were pooled yielding 12 mL of material with an A$_{280}$=0.219. This pooled $\alpha_2$M*/SK complex material was tested for endotoxin and found to contain <0.1 ng/mL at a concentration containing 1.0 $\mu$g/mL of SK.

In-vitro stimulation of PBMC was performed as follows: Cells from three healthy individuals (SW, HG, KW) were obtained as described above. One-hundred $\mu$L of cells (2×10$^6$/mL in Complete RPMI) was added to each well of a 96-well polystyrene tissue culture plate (Costar). For each plate, the top and bottom rows were not used for the assay but filled with 200 $\mu$L of sterile PBS. To each of quadruplicate wells was added 100 $\mu$L of SK (0.02–20 $\mu$g/mL media; four-fold dilutions) or $\alpha_2$M*/SK (0.002–2.0 $\mu$g/mL media; four-fold dilutions). Additional controls included $\alpha_2$M* alone (0.075–75 μg/mL media; four-fold dilutions) or PBS (0.04% –31% in media; four-fold dilutions). Duplicate plates were incubated for 5 and 6 days respectively at 37° C. in humidified, 5% CO2. For the last 6 hr of incubation, an additional 50 μL of media containing 0.5 μCi of $^3$H-thymidine (6.7 Ci/mmol in sterile H$_2$O; New England Nuclear) was added to each well. The contents of each well were harvested onto glass-fiber filters and washed using a Skatron automated cell harvester, the filters put into mini scintillation vials containing (3 mL of scintillant, and the incorporated radioactivity (expressed as counts per min [cpm]) determined by liquid scintillation spectrophotometry. Averages of quadruplicate samples were determined and plotted versus the concentration of SK or α2-macroglobulin*/SK.

There was no significant incorporation of $^3$H-thymidine by cells exposed to $α_2$M* alone or PBS as compared to historical data from cells exposed to media alone (data not shown). Similar results were obtained in another experiment using the same three donors. As illustrated in FIGS. 8–10, the peak proliferative response at 5 days to SK alone with cells obtained from SW, HG, and KW was observed at a concentration of 10 μg/mL SK, although the response by KW's cells was very low and essentially flat, suggesting that this individual was relatively anergic to SK.

Figure 11:
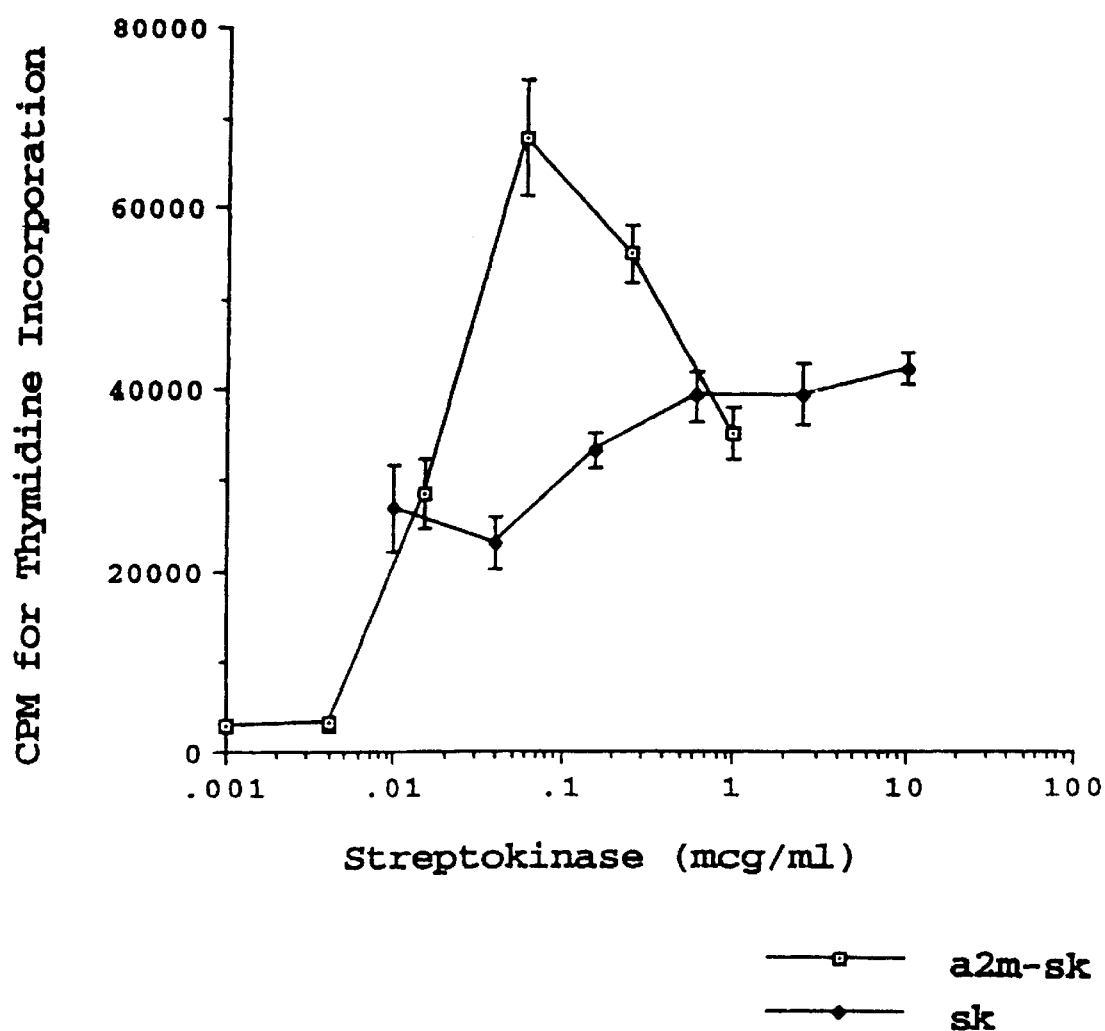
FIG. 11 depicts the same experiment as described for FIG. 8 with cells from individual SW, six days after exposure.
Figure 12:
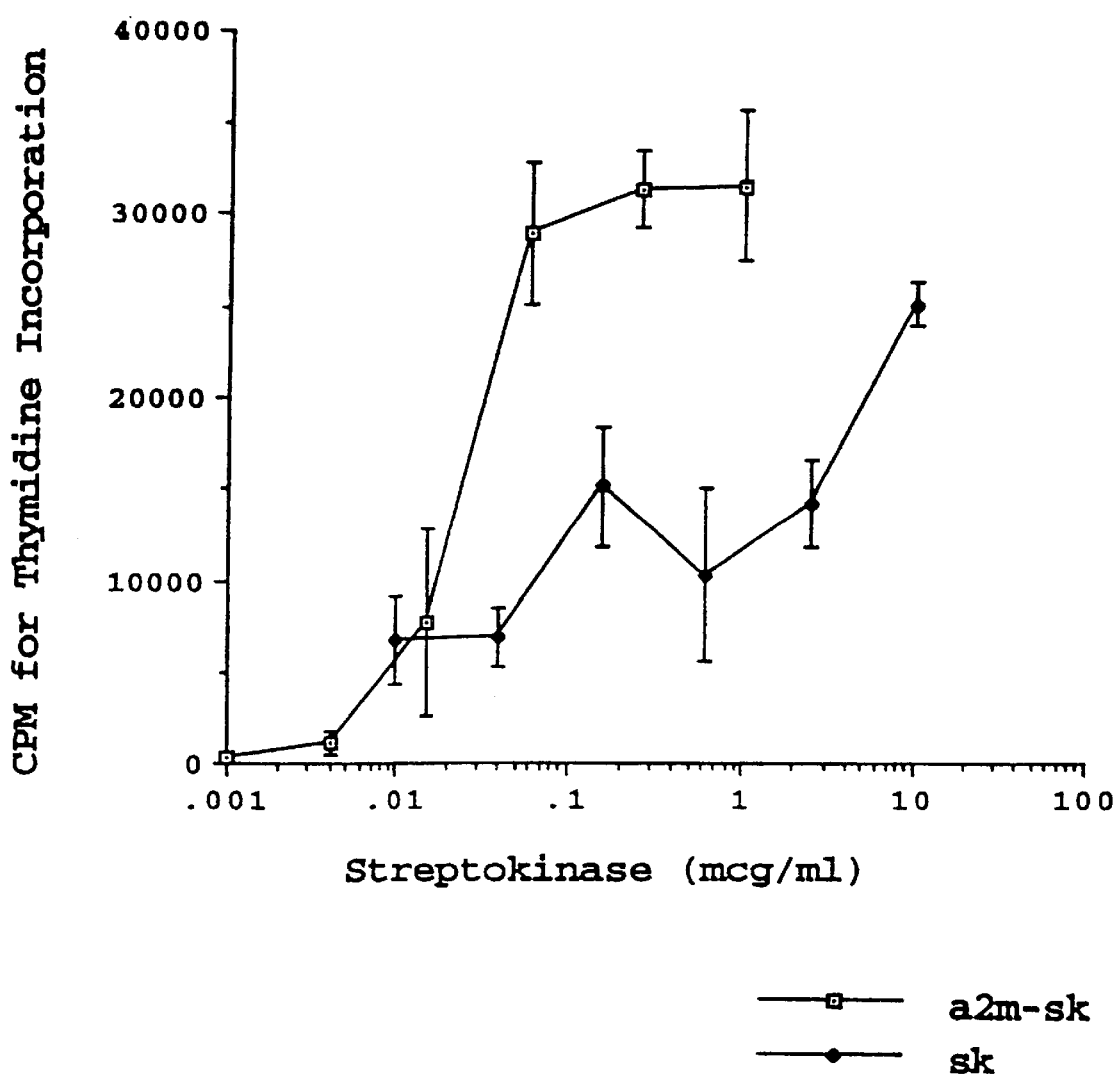
FIG. 12 depicts the same experiment as described for FIG. 8 with cells from individual HG, six days after exposure.
Figure 13:
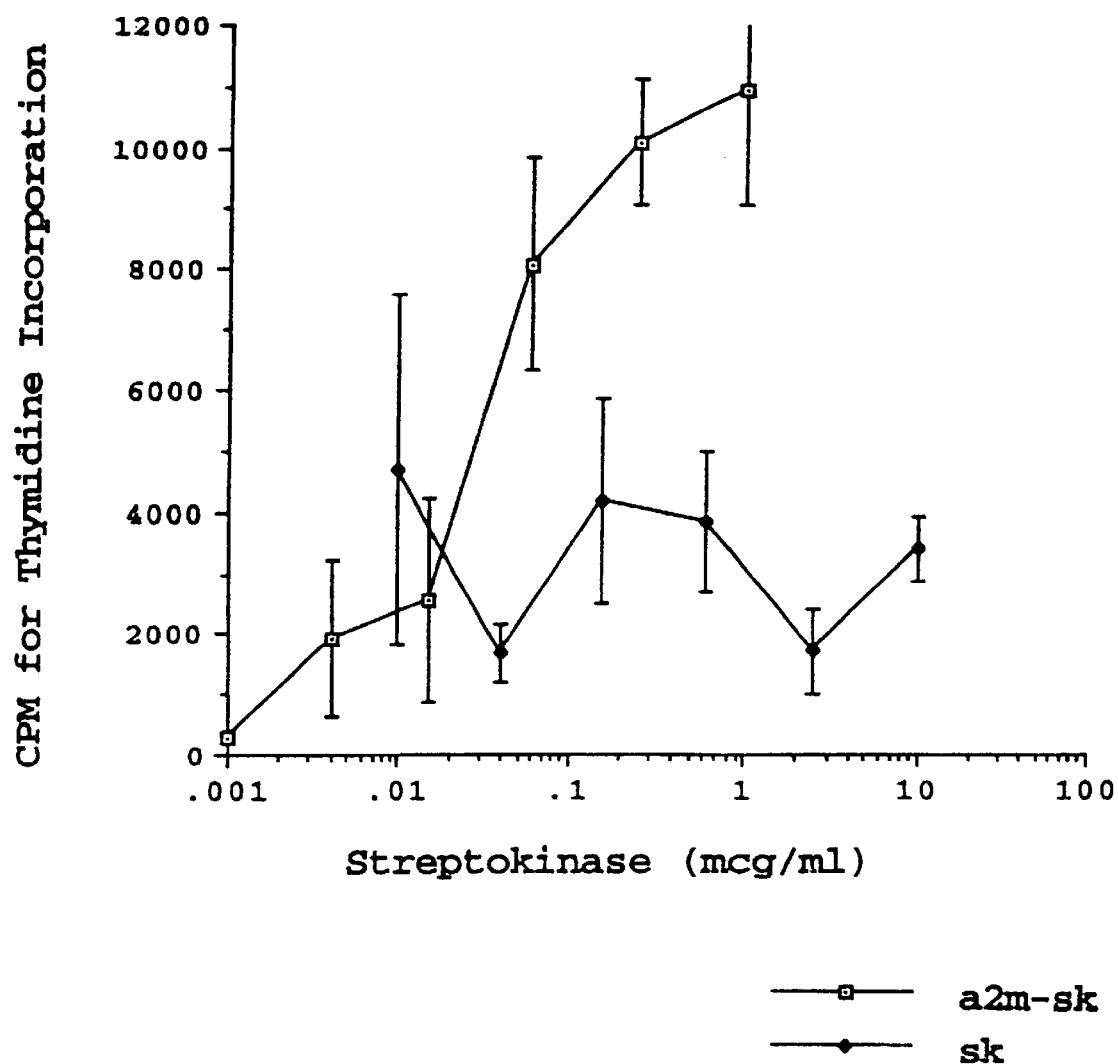
FIG. 13 depicts the same experiment as described for FIG. 8 with cells from individual KW, six days after exposure.

However, for each of the three cell donors, the maximal proliferative response at day 5 to 6 was 2–3 fold higher than that obtained with SK alone (FIGS. 8–10). In addition, for each of the three donors the maximal response observed with SK alone could be obtained with concentrations of $α_2$-macroglobulin*/SK complexes containing less than 1/300th the amount of SK. The day 6 results showed a similar pattern as for day 5 (FIGS. 11–13); although the peak response obtained for the complexes was still significantly higher than that observed for SK alone, the increase was not as pronounced as that observed on day 5. However, the concentration required to achieve peak proliferative responses was still dramatically lower (35-fold for SW; 200-fold for HG) with $α_2$-macroglobulin-SK complexes, and the cells from the essentially anergic donor (KW) again showed a distinct dose response to complexes where none was observed to SK alone. Thus the incorporation of SK into α2-macroglobulin* appears to significantly and dramatically increase the immunological response of cells already sensitized and to promote responses from cells either poorly sensitized or anergic.

EXAMPLE 10

The non-proteolytic, covalent incorporation of protein into a$_2$-macroglobulin* (a$_2$M*) is not limited to full-length, intact proteins. A hybrid synthetic peptide [T1-SP10MN(A); sequence= KQIINMWQEVGKAMYACTRPNYNKRKRI-HIGPGRAFYTTK; ref. 52] encoding a HIV (human immnunodeficiency virus) gp120 T-cell epitope (T1)(76) N-terminal to hydrophilic gp120 B-cell epitopes from the V3 loop region (SP10 sequences) (77–79) was synthesized by solid-phase synthesis and purified by RP-HPLC. The synthetic peptide was radiolabeled with $^{125}$I-Bolton-Hunter reagent (New England Nuclear) per manufacturer's instructions to a specific activity of approx. 132,000 cpm/mg of peptide. Human a$_2$M* was prepared as described above. To 470 μl of a$_2$M* (1072 pmol) was added 1000 μl of $^{125}$I-Bolton-Hunter labeled T1-SP10MN(A) (43130 pmol; 26×10$^6$ cpm). One-hundred and fifty μl of the mixture was removed for a parallel experiment to generate samples for analysis. The major portion of the mixture was incubated for 5 h at 50° C. In the parallel experiment, the 150 μl of the mixture removed above, as well as 150 μl of a$_2$M* in the absence of T1-SP10MN(A), were incubated at 50° C. and the samples were analyzed at 0, 5, and 24 h. After the mixture had been incubated 5 h at 50° C., free peptide was separated from peptide complexed with a$_2$M* by application of the mixture to a SEPHACRYL S300 HR (Sigma, St. Louis, Mo.) column (22.5 ml bed volume) equilibrated with 50 mM Tris-HCl, 50 mM NaCl, pH 7.5. The column was run at a flow rate of 5.4 ml/h and 1.8 ml fractions were collected. The absorbance$_{280nm}$ and the radioactivity was determined for each fraction. The amount of $^{125}$I-T1-SP10MN(A) bound to a$_2$M* in the a$_2$M*-$^{125}$I-T1-SP10MN(A) complex was determined from the radioactivity incorporated and the specific radioactivity of the $^{125}$I-T1-SP10MN(A) used for complex formation. Column fractions were analyzed by electrophoresis on 4–15% pore limit gels and on 4–20% SDS PAGE in the presence or absence of the reducing agent dithiothreitol (DTT). The level of covalent binding was quantified by denaturing the a$_2$M*-containing fractions in SDS-PAGE sample buffer for 5 min at 100° C. followed by electrophoresis. On SDS-PAGE, approximately 6.4 moles of $^{125}$I-T1-SP10MN(A) bound per mole of a$_2$M* in the absence of DTT while approximately 1.4 moles of $^{251}$I-T1-SP10MN (A) bound in the presence of DTT.

Thus, the complex had 5 mol of peptide bound covalently to each mol of $α_2$M*. Under reducing conditions, approximately 1 mol of peptide remained bound per mol of $α_2$M*. The stoichiometry for a peptide incorporation is slightly enhanced over the proteins mentioned above, insulin and lysozyme, probably due to the dimerization of the peptide. The peptide has only one cysteinyl residue and analysis by non-reduced SDS-PAGE confirmed that a fraction of the peptide is present in the form of a disulfide-linked dimer.

EXAMPLE 11

The non-proteolytic, covalent incorporation of a synthetic peptide into a$_2$-macroglobulin* (a$_2$M*) was confirmed with a second HIV-encoded peptide. A hybrid synthetic peptide [T1-SP10IIIB(A); sequence= KQIINMWQEVGKAMYACTRPNNNTRK-SIRIQRGPGRAFVTI; ref. 52; SEQ ID NO:2] encoding a HIV (human immunodeficiency virus) gp120 T-cell epitope (T1) (ref. 76) N-terminal to hydrophilic gp120B-cell epitopes from the V3 loop region (SP10 sequences) (ref. 77–79) was synthesized by solid-phase synthesis and purified by RP-HPLC. The synthetic peptide was radiolabeled with $^{125}$I-Bolton-Hunter reagent (New England Nuclear) per manufacturer's instructions to a specific activity of approx. 2×10$^7$ cpm/mg of peptide and diluted with unlabeled peptide prior to incorporation into a$_2$M*. Human a$_2$M* was prepared as described above. To 470 μl of a$_2$M* (69 pmol) was added 1000 μl of $^{125}$I-Bolton-Hunter labeled T1-SP10IIIB(A) (2778 pmol; approx.3.4×10$^6$ cpm). One-hundred and fifty μl of the mixture was removed for a parallel experiment to generate samples for analysis. The major portion of the mixture was incubated for 5 h at 50° C. After the mixture had been incubated 5 h at 50° C., free peptide was separated from peptide complexed with a$_2$M* by application of the mixture to a Sephacryl S300 HR (Sigma, St. Louis, Mo.) column (22.5 ml bed volume) equilibrated with 50 mM Tris-HCl, 50 mM NaCl, pH 7.5. The column was run at a flow rate of 5.4 ml/h and 1.8 ml fractions were collected. The absorbance$_{280nm}$ and the radioactivity was determined for each fraction. The amount of $^{125}$I-T1-SP10IIIB(A) bound to a$_2$M* in the a$_2$M*-$^{125}$I-T1-SP10IIIB(A) complex was determined from the radioactivity incorporated and the specific radioactivity of the $^{125}$I-T1-SP10IIIB(A) used for complex formation. Column fractions were analyzed by electrophoresis on 4–15% pore limit gels and on 4–20% SDS PAGE in the presence or absence of the reducing agent dithiothreitol (DTT). The level of covalent binding was quantified by denaturing the $a_2M^*$-containing fractions in SDS-PAGE sample buffer for 5 min at 100° C. followed by electrophoresis. On SDS-PAGE, approximately 6.5 moles of $^{125}$I-T1-SP10IIIB(A)) bound per mole of $a_2M^*$ in the absence of DTT while approximately 1.1 moles of $^{125}$I-T1-SP10IIIB (A) bound in the presence of DTT.

EXAMPLE 12

In addition to the above-cited examples, additional proteins or synthetic peptides which are non-proteolytically and covalently incorporated into $a_2$-macroglobulin* to form an immunogen of the present invention following procedures similar to those above include HBsAg, the protein representing one of the major surface antigens of human Hepatitis B Virus; peptide OS (amino acids 124–147 of HBsAg; sequence=CTTPAQGNSMFPSCCCTKPTDGNC; SEQ ID NO:3)(80); and a chimeric peptide (sequence= TRILTIPQSLDSCTKPTDGNC; SEQ ID NO:4)(81) representing a T-cell epitope (amino acids 23–34) of HBsAg joined to the NH$_2$-terminus of a B-cell epitope (amino acids 139–147) of HBsAg.

In the example of HBsAg, the recombinant protein produced in yeast (Advanced Biotechnologies Inc., Columbia, Md.) was analyzed using PAGE (polyacrylamide gel electrophoresis) and SDS-PAGE, under reducing and non-reducing conditions. It was determined that the protein was aggregated and that the aggregation was disulfide bond dependent. In order to reduce the protein to its monomeric state (ca. 25 kDa) the protein was reduced and alkylated as follows. HBsAg was first desalted using a PD-10 or similar (Pharmacia Biotech) column equilibrated in 50 mM Tris-HCl, 100 mM NaCl, pH 8. The following step was then performed in the dark by wrapping the tube in aluminum foil. The protein was reduced by adding 1 mM DTT for 30 min at 37° C. The reduced protein was then alkylated by adding 5 mM iodoacetamide followed by a 30 min incubation at 37° C. Following completion of the reaction the reduced/alkylated HBsAg was desalted using a PD-10 or similar column equilibrated in 50 mM Tris-HCl, 100 mM NaCl. pH 7.4. HBsAg was incorporated into both human $a_2M^*$ and mouse $a_2M^*$, prepared as described above, by incubation of the reduced/alkylated HBsAg with the $a_2M^*$ preparations (40:1 molar ratio of HBsAg to $a_2M^*$) for 5 h at 50° C. The incubation mixtures were then separated on PAGE and SDS-PAGE gels, under reducing and non-reducing conditions, and transferred to PVDF membranes by Western blotting. The membranes were then blocked for non-specific binding and incubated with a rabbit polyclonal antibody to HBsAg to determine the presence and size of HBsAg. This analysis verified that a portion of the HBsAg was associated with $a_2M^*$.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

The following is a listing of the publications referred to in the foregoing specification, with numbers corresponding to those presented herein above. Each of the following references, as well as the references cited throughout this specification, is hereby incorporated herein in its entirety.

1. Lanzavecchia, A. 1990. Receptor-mediated antigen uptake and its effect on antigen presentation to class II-restricted T lymphocytes. *Annu. Rev. Immunol.* 8:773.
2. Fossum, S., S. F. Berg, and S. Mjaaland. 1992. Targeting antigens to antigen presenting cells. *Semin. in Immunol.* 4:275.
3. Su, D., and N. van Rooijen. 1989. The role of macrophages in the imnmunoadjuvant action of liposomes: Effects of elimination of splenic macrophages on the immune response against intravenously injected liposome-associated albumin antigen. *Immunology* 66:466.
4. Verma, J., M. Rao, S. Amselem, U. Krzych, C. R. Alving, S. J. Green, and N. M. Wassef. 1992. Adjuvant effects of liposomes containing lipid A: Enhancement of liposomal antigen presentation and recruitment of macrophages. *Infection and Immunily* 60:2438.
5. Kawamura, H., and J. A. Berzofsky. 1986. Enhancement of antigenic potency in vitro and immunogenicity in vivo by coupling the antigen to anti-immunoglobulin. *J. Immunol.* 136:58.
6. Carayanniotis, G., and B. H. Barber. 1987. Adjuvant-free IgG responses induced with antigen coupled to antibodies against class II MHC. *Nature* 327:59.
7. Casten, L. A., and S. K. Pierce. 1988. Receptor-mediated B cell antigen processing: Increased antigenicity of a globular protein covalently coupled to antibodies specific for B cell surface structures. *J. Immunol.* 140:404.
8. Snider, D. P., A. Kaubisch, and D. M. Segal. 1990. Enhanced antigen immunogenicity induced by bispecific antibodies. *J. Exp. Med.* 171:1957.
9. Mjaaland, S., and S. Fossum. 1991. Antigen targeting with monoclonal antibodies as vectors II. Further evidence that conjugation of antigen to specific monolonal antibodies enhances uptake by antigen presenting cells. *Int. Immunol.* 3:1315.
10. Manca, F., D. Fenogijo, G. LiPira, A. Kunki, and F. Celada. 1991. Effect of antigen/antibody ratio on macrophage uptake, processing, and presentation to T cells of antigen complexed with polyclonal antibodies. *J. Exp. Med.* 173:37.
11. Gontijo, C. M., and G. Möller. 1991. Membrane-incorporated immunoglobulin receptors increase the antigen-presenting ability of B cells. *Scand. J. Immunol.* 34:577.
12. Stockinger, B. 1992. Capacity of antigen uptake by B cells, fibroblasts or macrophages determines efficiency of presentation of a soluble self antigen (C5) to T lymphocytes. *Eur. J. Immunol,* 22:1271.
13. Rock. K. L., B. Benacerraf, and A. K. Abbas. 1984. Antigen presentation by hapten-specific B lymphocytes I. Role of surface immunoglobulin receptors. *J. Exp. Med.* 160:1102.
14. Lanzavecchia, A. 1985. Antigen-specific interaction between T and B cells. *Nature* 314:537.
15. Unanue (1981), *Adv. Immunol.* 31:1–136.
16. Lorenz, R. G., J. S. Blum, and P. M. Allen. 1990. Constitutive competition by self proteins for antigen presentation can be overcome by receptor-enhanced uptake. *J. Immunol.* 144:1600.
17. Arvieux, J., H. Yssel, and M. G. Colomb. 1988. Antigen-bound C3b and C4b enhance antigen-presenting cell function in activation of human T-cell clones. *Immunol.* 65:229.
18. Gron, H., Thogersen, I. B., Enghild, J. J. and Pizzo, S. V. (1996) *Biochem. J.* 318, 539–545

19. Salvesen, G. S., and A. J. Barrett. 1980. Covalent binding of proteinases in their reaction with $\alpha_2$-macroglobulin. *Biochem. J.* 187:695.
20. Salvesen, G. S., C. A. Sayers, and A. J. Barrett. 1981. Further characterization of the covalent linking reaction of $\alpha_2$-macroglobulin. *Biochem. J.* 195:453.
21. Chu, C. T., D. S. Rubenstein, J. J. Enghild, and S. V. Pizzo. 1991. Mechanism of insulin incorporation into $\alpha_2$-macroglobulin: Implications for the study of peptide and growth factor binding. *Biochemistry* 30:1551.
22. Hovi, T., D. Mosher, and A. Vaheri. 1977. Cultured human monocytes synthesize and secrete $\alpha_2$-macroglobulin. *J. Exp. Med.* 145:1580.
23. Cohn, Z. A. 1978. The activation of mononuclear phagocytes: Fact, fancy, and future. *J. Immunol.* 121:813.
24. Schlesinger, C., J. McEntire, J. Wallman, J. L. Skosey, W. C. Hanley, and M. Teodorescu. 1989. Covalent binding to $\alpha$-macroglobulins if a protein with free SH groups produced by activated B cells: blocking by D-penicillamine and gold compounds. *Mol. Immunol.* 26:255.
25. Borth, W., B. Scheer, A. Urbansky, T. A. Luger, and L. Sottrup-Jensen. 1990. Binding of IL-1$\beta$ to $\alpha$-macroglobulins and release by thioredoxin. *J. Immunol.* 145:3747.
26. Teodorescu, M., M. McAffee, J. L. Skosey, J. Wallman, A. Shaw, and W. C. Hanly. 1991. Covalent disulfide binding of human IL-1$\beta$ to $\alpha_2$-macroglobulin: Inhibition by D-penicillamine. *Mol. Immunol.* 28:323.
27. Chu, C. T., and S. V. Pizzo, 1993. Receptor-mediated antigen delivery into macrophages: Complexing antigen to $\alpha_2$-macroglobulin enhances presentation to T-cells. *J. Immunol.* 150:48.
28. Ito, F., S. Ito, and N. Shimizu. 1984. Transmembrane delivery of polypeptide hormones bypassing the intrinsic cell surface receptors: A conjugate of insulin with $\alpha_2$-macroglobulin ($\alpha_2$M) recognizing both insulin and $\alpha_2$Mreceptors and its biological activity in relation to endocytic pathways. *Mol. Cell. Endocrin.* 36:165.
29. Osada, T., Y. Kuroda, and A. Ikai. 1987. Endocytotic internalization of $\alpha_2$-macroglobulin: $\alpha$-galactosidase conjugate by cultured fibroblasts derived from Fabry hemizygote. *Biochem. Biophys. Res. Commun.* 142:100.
30. Kaplan, J., and M. L. Nielsen. 1979. Analysis of macrophage surface receptors. Binding of $\alpha$-macroglobulin-proteinase complexes to rabbit alveolar macrophages. *J. Biol. Chem.* 254:7323.
31. Sottrup-Jensen, L., T. E. Petersen, and S. Magnusson. 1981. Trypsin-induced activation of the thiol esters in $\alpha_2$-macroglobulin generates a short-lived intermediate ('nascent' $\alpha_2$M) that can react rapidly to incorporate not only methylamine or putrescine but also proteins lacking proteinase activity. *FEBS Lett.* 128:123.
32. Sottrup-Jensen, L. 1987. $\alpha_2$-Macroglobulin and related thiol ester plasma proteins. In *The Plasma Proteins: Structure, Function, and Genetic Control*, Vol. V. F. W. Putnams, ed. Academic Press, Inc., Orlando, Fla., p. 191.
33. Harrison, R. A. 1984. The family of proteins having internal thiolester bonds. *Recent Advances in Immunology* 17:87
34. Feldman, S. R., S. L. Gonias, and S. V. Pizzo. 1985. Model of a$_2$-macroglobulin structure and function. *Proc. Natl. Acad. Sci. USA* 82:5700.
35. Barrett, A. J., and P. M. Starkey. 1973. The interaction of $\alpha_2$-macroglobulin with proteinases: Characteristics and specificity of the reaction, and a hypothesis concerning its molecular mechanism. *Biochem. J.* 133:709.
36. Pizzo, S. V., and S. L. Gonias. 1984. Receptor-mediated protease regulation. In *The Receptors*, Vol. I P. M. Conns, ed. Academic Press, Orlando, Fla., p. 177.
37. Sottrup-Jensen, L. 1989. $\alpha$-Macroglobulins: structure, shape and mechanism of proteinase complex formation. *J. Biol. Chem.* 263:11539.
38. Herz, J., U. Hamann, S. Rogne, O. Myklebost, H. Gausepohl, and K. K. Stanley. 1988. Surface location and high affinity for calcium of a 500-kDa liver membrane proteins closely related to the LDL-receptor suggest a physiological role as lipoprotein receptor. *EMBO J.* 7:4119.
39. Strickland, D. K., J. D. Ashcom, S. Williams, W. H. Burgess, M. Migliorini, and W. S. Argraves. 1990. Sequence identity between the $\alpha_2$-macroglobulin receptor and low density lipoprotein receptor-related protein suggests that this molecule is a multifunctional receptor. *J. Biol. Chem.* 265:17401.
40. Pizzo, S. V. 1988. Receptor recognition of the plasma proteinase inhibitor $\alpha_2$-macroglobulin. *ISI Atlas of Science: Biochemistry* 1:242.
41. Enghild, J. J., I. B. Thøgersen, P. A. Roche, and S. V. Pizzo. 1989. A conserved region in $\alpha$-macroglobulins participates in binding to the mammalian $\alpha$-macroglobulin receptor. *Biochemistry* 28:1406.
42. LaMarre, J., M. A. Hayes, G. K. Wollenberg, I. Hussaini, S. W. Hall, and S. L. Gonias. 1991. An $\alpha_2$-macroglobulin receptor-dependent mechanism for the plasma clearance of transforming growth factor-$\beta$1 in mice. *J. Clin. Invest.* 87:39.
43. Osada et al. (1987), *Biochem. Biophys. Res. Com.* 146(1):26–31.
44. Osada et al. (1988), *Biochem. Biophys. Res. Com.* 150(2):883–889.
45. Ito et al. (1983), *FEBS Letters*, 152(1):131–135
46. Osada et al., (1987), *Biochem. Biophys. Res. Com.* 142(1):100–106.
47. Osada et al. (1987), *Biochem. Biophys. Res. Com.* 143(3):954–958
48. James, K. 1980. Alpha$_2$ macroglobulin and its possible importance in immune systems. *Trends Biochem. Sci.* 5:43.
49. Salvesen et al. 1981, *Biochem J.* 195:453–61
50. Van Leuven et al., 1982, *Biochem J.* 201:119–28.
51. Van Rompaey et al., 1995, *Biochem. J.* 312:183–90.
52. Hart et al. ((1991), *PROC. NATL. ACAD. SCI. U.S.A.* 88:9448–52.
53. Salvesen, G., and J. J. Enghild. $\alpha$-Macroglobulins: Detection and characterization. *Methods Enzymol.* 223:121.
54. Habeeb, A. F. S. A. (1972) Methods Enzymol. 25, 457–464
55. Hall, P. K., and R. C. Roberts. 1978. Physical and chemical properties of human plasma $\alpha_2$-macroglobulin. *Biochem. J.* 171:27.
56. Salvesen, G. and Nagase, H. (1989) in Proteolytic Enzymes: A Practical Approach (Beyton, R. J. and Bond, J. S., eds.) pp 83–104, IRL Press at Oxford University Press, New York
57. Enghild, J. J., I. B. Thøgersen, G. Salvesen, G. H. Fey, N. L. Figler, S. L. Gonias, and S. V. Pizzo. 1990. $\alpha$-Macroglobulin from *Limulus polyphemus* exhibits proteinase inhibitory activity and participates in a hemolytic system. *Biochemistry* 29:10070.
58. Praissman, M. and Rupley, J. A. (1968) Biochemistry 7, 2431–2445
59. Canfield, R. E. 1963. Peptides derived from tryptic digestion of egg white lysozyme. *J. Biol. Chem.* 238:2691.

60. Bolton, A. E. and Hunter, W. M. (1973) Biochemistry Journal 133, 529–539
61. Bury, A. F. 1981. Analysis of protein and peptide mixtures: Evaluation of three sodium dodecyl sulphate-polyacrylamide gel electrophoresis buffer systems. *J. Chromatogr.* 213:491.
61b. Swenson, R. P. and Howard J. B. (1979) Proc. Natl. Acad. Sci. USA 76: 4313–4316.
62. Howard, J. B., Vermeulen, M., and Swenson, R. P. (1980) J. Biol. Chem. 20 255: 3820–3823.
63. Van Leuven, F., Cassiman, J-J. and Van den Berghe, H. (1981) J. Biol. Chem. 256, 9016–9022
64. Imber, M. J., and S. V. Pizzo. 1981. Clearance and binding of two electrophoretic "fast" forms of human $\alpha_2$-macroglobulin. *J. Biol. Chem.* 256:8134.
65. Misra, U. K., C. T. Chu, D. S. Rubenstein, G. Gawdi, and S. V. Pizzo. 1993. Receptor-recognized $\alpha_2$-macroglobulin-methylamine elevates intracellular calcium, inositol phosphates and cyclic AMP in murine peritoneal macrophages. *Biochem. J.* 290:885.
66. Jensen, P. E. H., Shanbhag, V. P. and Stigbrand, T. (1995) Eur. J. Biochem. 227, 612–616
67. Jensen, P. E. H. and Stigbrand, T. (1992) Eur. J. Biochem. 210, 1071–1077
68. Bjork, I. (1985) Biochem. J. 231, 451–457
69. Cunningham, L. W., Crews, B. C. and Gettins, P. (1990) Biochemistry 29, 1638–1643
70. Van Leuven, F., Marynen, P., Cassiman, J-J. and Van den Berghe, H. (1982) Biochem. J. 203, 405–411
71. Gettins, P. G. W. (1995) Biochemistry 34, 12233–12240
72. Howard, G. C., Misra, U. K., DeCamp, D. L. and Pizzo, S. V. (1995) J. Clin. Invest. 97, 1193–1203
73. Gettins, P. G. W. and Crews, B. C. (1994) Ann. N. Y. Acad. Sci. 737, 383–398
74. Chu, C. T. and Pizzo, S. V. (1994) Lab. Invest. 71, 792–812
75. Travis, J., and G. S. Salvesen. 1983. Human plasma proteinase inhibitors. *Ann. Rev. Biochem.* 52:655.
76. Cease, K. B., Margalit, H., Cornette, J. L., Putney, S. D., Robey, W. G., Ouyang, C., Streicher, H. Z., Fischinger, P. J., Gallo, R. C., Delisi, C., and Berzofsky, J. A. (1987) Proc. Natl. Acad. Sci., USA 84:4249–4253
77. Palker, T. J., Clark, M. E., Langlois, A. J., Matthews, T. J., weinhold, K. J., Randall, R. R., Bolognesi, D. P., and Haynes, B. F. (1988) Proc. Natl. Acad. Sci., USA 85:1932–1936
78. Palker, T. J., Matthews, T. J., Langlois, A. J., Tanner, M. E., Martin, M. E., Scearce, R. M., Kimn, J. E., Berzofsky, J. A., Bolognesi, D. P., and Haynes, B. F. (1989) J. Immunol. 142:3612–3619
79. Hart, M. K., Palker, T. J., Matthews, T. J., Langlois, A. J., Lerche, N. W., Martin, M. E., Scearce, R. M., McDanal, C., Bolognesi, D. P., and Haynes, B. F. (1990) J. Immunol. 145:2677–2685
80. Mishra, A., Rao, K. V. S., Durgapal, H., Manivel, V., and Panda, S. K. (1993) Immunol. 79:362–367
81. Steward, M. W., Partidos, C. D., D'Mello, F. and Howard, C. R. (1993) Vaccine 11:1405–1414

What is claimed is:

1. A stable complex comprising at least one intact biomolecule having a nucleophilic group and activated $\alpha_2$-microglobulin having an intact bait region, wherein said intact biomolecule having a nucleophilic group is bound to said activated $\alpha_2$-macroglobulin through a bond consisting of said nucleophilic group covalently bound to a γ-glutamyl group of a cleaved thiol ester of said activated $\alpha_2$-macroglobulin.

2. The stable complex of claim 1 wherein said biomolecule is selected from the group consisting of peptides, proteins, carbohydrates, cytokines, growth factors, hormones, enzymes, toxins, anti-sense RNA, drugs, oligonucleotides, lipids, DNA, antigens, immunogens, allergens, and combinations thereof.

3. The stable complex of claim 2 wherein said biomolecule is selected from the group consisting of KQIINMWQEVGKAMYACTRPNYNKRKRIHIGPGRAFYTTK (SEQ ID NO: 1); KQIINMWQEVGKAMYACTRPNNNTRKSIRIQRGPGRAFVTI (SEQ ID NO:2); CTTPAQGNSMFPSCCCTKPTDGNC (SEQ ID NO:3); and TRILTIPQSLDSCTKPTDGNC (SEQ ID NO:4).

4. The stable complex of claim 1 wherein said biomolecule has a molecular weight of from about 0.5 kilodaltons to about 100 kilodaltons.

5. An immunogen comprising the stable complex of claim 1, wherein said at least one intact biomolecule having a nucleophilic group consists of an antigenic molecule having at least one epitope.

6. The stable complex of claim 2 wherein said antigen is selected from the group consisting of HIV antigens, hepatitis virus antigens, peptides thereof, fragments thereof, hybrid peptides thereof, chimeric peptides thereof, and hybrid synthetic peptides thereof.

7. The stable complex of claim 6 wherein said HIV antigens or fragments thereof comprises gp120, gp160, or a fragment thereof.

8. The stable complex of claim 6 wherein said hepatitis virus antigens or fragments thereof comprises HbsAg or a fragment thereof.

9. A stable complex comprising at least one intact biomolecule having a nucleophilic group and activated $\alpha_2$-macroglobulin having an intact bait region, wherein said intact biomolecule having a nucleophilic group is bound to said activated $\alpha_2$-macroglobulin through a bond consisting of said nucleophilic group covalently bound to a γ-glutamyl group of a cleaved thiol ester of said activated $\alpha_2$-macroglobulin, said complex prepared by the sequential steps of activating $\alpha_2$-macroglobulin by incubation with a nucleophilic compound to form nucleophile-activated $\alpha_2$-macroglobulin, removing excess said nucleophilic compound, and incubating said nucleophile-activated $\alpha_2$-macroglobulin with said biomolecule having a nucleophilic group, for a period of time sufficient wherein said stable complex is formed.

10. The stable complex of claim 9 wherein said biomolecule is selected from the group consisting of peptides, proteins, carbohydrates, cytokines, growth factors, hormones, enzymes, toxins, anti-sense RNA, drugs, oligonucleotides, lipids, DNA, antigens, immunogens, allergens, and combinations thereof.

11. The stable complex of claim 10 wherein said antigen is selected from the group consisting of HIV antigens, hepatitis virus antigens, peptides thereof, fragments thereof, hybrid peptides thereof, chimeric peptides thereof, and hybrid synthetic peptides thereof.

12. The stable complex of claim 11 wherein said HIV antigens or fragments thereof comprises gp120, gp160, or a fragment thereof.

13. The stable complex of claim 11 wherein said hepatitis virus antigens or fragments thereof comprises HbsAg or a fragment thereof.

14. The stable complex of claim 9 wherein said biomolecule is selected from the group consisting of KQIINMWQEVGKAMYACTRPNYNKRKRIHIGPGRAFYTTK (SEQ ID NO:1); KQIINMWQEVGKAMYACTRPNNNTRKSIRIQRGPGRAFVTI (SEQ ID NO:2); CTTPAQGNSMFPSCCCTKPTDGNC (SEQ ID NO:3); and TRILTIPQSLDSCTKPTDGNC (SEQ ID NO:4).

15. The stable complex of claim 9 wherein said biomolecule has a molecular weight of from about 0.5 kilodaltons to about 100 kilodaltons.

16. An immunogen comprising an antigenic molecule having at least one epitope in a complex with $\alpha_2$-macroglobulin, said immunogen comprising the stable complex of claim 9.

17. The stable complex of claim 9 wherein said nucleophilic compound has the formula $RNH_2$, wherein R is selected from the group consisting of hydrogen and an alkyl group of 1 to 6 carbon atoms.

18. The stable complex of claim 17 wherein said nucleophilic compound is selected from the group consisting of ammonia, methylamine, ethylamine, and combinations thereof.

19. The stable complex of claim 9 wherein said incubating of said nucleophile-activated $\alpha_2$-macroglobulin with said biomolecule is carried out at a temperature ranging from about 35° C. to about 55° C.

20. The stable complex of claim 9 wherein said incubation step is carried out at a temperature ranging from about 37° C. to about 50° C., and a period of time ranging from about 1 hour to about 24 hours.

21. The stable complex of claim 20 wherein the temperature and time ranges of said incubation are selected from a temperature of about 37° C. for about 24 hours, and a temperature of about 50° C. from about 1 to about 5 hours.

22. A method for the preparation of a covalent complex between at least one intact biomolecule having a nucleophilic group and activated $\alpha_2$-macroglobulin having an intact bait region, wherein said intact biomolecule having a nucleophilic group is bound to said activated $\alpha_2$-macroglobulin through a bond consisting of said nucleophilic group covalently bound to a $\gamma$-glutamyl group of a cleaved thiol ester of said activated $\alpha_2$-macroglobulin, said method comprising the steps of
  i) activating $\alpha_2$-macroglobulin by incubation with a nucleophilic compound to form activated $\alpha_2$-macroglobulin;
  ii) removing excess said nucleophilic compound; and
  iii) incubating said activated $\alpha_2$-macroglobulin with said biomolecule having a nucleophilic group for a period of time sufficient to form said complex.

23. The method of claim 22 wherein said nucleophilic compound has the formula $RNH_2$, wherein R is selected from the group consisting of hydrogen and an alkyl group of 1 to 6 carbon atoms.

24. The method of claim 23 wherein said nucleophilic compound is selected from the group consisting of ammonia, methylamine, ethylamine, and combinations thereof.

25. The method of claim 22 wherein said incubating of said nucleophile-activated $\alpha_2$-macroglobulin with said biomolecule is carried out at a temperature ranging from about 35° C. to about 55° C.

26. The method of claim 22 wherein said incubation step is carried out at a temperature ranging from about 37° C. to about 50° C., and a period of time ranging from about 1 hour to about 24 hours.

27. The method of claim 26 wherein the temperature and time ranges of said incubation are selected from a temperature of about 37° C. for about 24 hours, and a temperature of about 50° C. from about 1 to about 5 hours.

28. The method of claim 22 wherein said biomolecule is selected from the group consisting of peptides, proteins, carbohydrates, cytokines, growth factors, hormones, enzymes, toxins, anti-sense RNA, drugs, oligonucleotides, lipids, DNA, antigens, immunogens, allergens, and combinations thereof.

29. The method of claim 28 wherein said antigen is selected from the group consisting of HIV antigens, hepatitis virus antigens, peptides thereof, fragments thereof, hybrid peptides thereof, chimeric peptides thereof, and hybrid synthetic peptides thereof.

30. The method of claim 29 wherein said HIV antigens or fragments thereof comprises gp120, gp160, or a fragment thereof.

31. The method of claim 29 wherein said hepatitis virus antigens or fragments thereof comprises HbsAg or a fragment thereof.

32. The method of claim 28 wherein said biomolecule is selected from the group consisting of KQIINMWQEVGKAMYACTRPNYNKRKRIHIGPGRAFYTTK (SEQ ID NO:1); KQIINMWQEVGKAMYACTRP-NNNTRKSIRIQRGPGRAFVTI (SEQ ID NO:2); CTTPAQGNSMFPSCCCTKPTDGNC (SEQ ID NO:3); and TRILTIPQSLDSCTKPTDGNC (SEQ ID NO:4).

33. The method of claim 5 wherein the molecular weight of said biomolecule is from about 0.5 kilodaltons to about 100 kilodaltons.

34. The method of claim 22 wherein said method is carried out in the absence of a proteolytic enzyme capable of cleaving said biomolecule and said bait region.

35. An immunogen comprising a biomolecule having a nucleophilic group in a complex with $\alpha_2$-macroglobulin having an intact bait region, said biomolecule having a nucleophilic group having at least one epitope, wherein said activated $\alpha_2$-macroglobulin is capable of binding a receptor for $\alpha_2$-macroglobulin, said complex comprising at least one intact biomolecule having a nucleophilic group and activated $\alpha_2$-macroglobulin with an intact bait region, wherein said intact biomolecule having a nucleophilic group is bound to said activated $\alpha_2$-macroglobulin through a bond consisting of said nucleophilic group covalently bound to a $\gamma$-glutamyl group of a cleaved thiol ester of said activated $\alpha_2$-macroglobulin.

36. The immunogen of claim 35 wherein said biomolecule is selected from the group consisting of peptides, proteins, carbohydrates, cytokines, growth factors, hormones, enzymes, toxins, anti-sense RNA, drugs, oligonucleotides, lipids, DNA, antigens, immunogens, allergens, and combinations thereof.

37. The immunogen of claim 36 wherein said antigen is selected from the group consisting of HIV antigens, hepatitis virus antigens, peptides thereof, fragments thereof, hybrid peptides thereof, chimeric peptides thereof, and hybrid synthetic peptides thereof.

38. The immunogen of claim 37 wherein said HIV antigens or fragments thereof comprises gp120, gp160, or a fragment thereof.

39. The immunogen of claim 37 wherein said hepatitis virus antigens or fragments thereof comprises HbsAg or a fragment thereof.

40. The immunogen of claim 35 wherein said biomolecule is selected from the group consisting of KQIINMWQEVGKAMYACTRPNYNKRKRIHIGPGRAFYTTK (SEQ ID NO:1); KQIINMWQEVGKAMYACTRP-NNNTRKSIRIQRGPGRAFVTI (SEQ ID NO:2); CTTPAQGNSMFPSCCCTKPTDGNC (SEQ ID NO:3); and TRILTIPQSLDSCTKPTDGNC (SEQ ID NO:4).

41. The immunogen of claim 35 wherein said biomolecule has a molecular weight of from about 0.5 kilodaltons to about 100 kilodaltons.

42. A vaccine comprising a stable complex comprising at least one intact biomolecule having a nucleophilic group and activated $\alpha_2$-macroglobulin having an intact bait region, wherein said intact biomolecule having a nucleophilic group is bound to said activated $\alpha_2$-macroglobulin through a bond consisting of said nucleophilic group covalently bound to a $\gamma$-glutamyl group of a cleaved thiol ester of said activated $\alpha_2$-macroglobulin, said $\alpha_2$-macroglobulin capable of binding a receptor for $\alpha_2$-macroglobulin.

43. The vaccine of claim 42 wherein said biomolecule is selected from the group consisting of peptides, proteins, carbohydrates, cytokines, growth factors, hormones, enzymes, toxins, anti-sense RNA, drugs, oligonucleotides, lipids, DNA, antigens, immunogens, allergens, and combinations thereof.

44. The vaccine of claim 43 wherein said antigen is selected from the group consisting of HIV antigens, hepatitis virus antigens, peptides thereof, fragments thereof, hybrid peptides thereof, chimeric peptides thereof, and hybrid synthetic peptides thereof.

45. The vaccine of claim 44 wherein said HIV antigens or fragments thereof comprises gp120, gp160, or a fragment thereof.

46. The vaccine of claim 44 wherein said hepatitis virus antigens of fragments thereof comprises HbsAg or a fragment thereof.

47. The vaccine of claim 42 wherein said biomolecule is selected from the group consisting of KQIINMWQEVGKAMYACTRPNYNKRKRIHIGPGRAFYTTK (SEQ ID NO:1); KQIINMWQEVGKAMYACTRPNNNTRKSIRIQRGPGRAFVTI (SEQ ID NO:2); CTTPAQGNSMFPSCCCTKPTDGNC (SEQ ID NO:3); and TRILTIPQSLDSCTKPTDGNC (SEQ ID NO:4).

48. The vaccine of claim 42 wherein said biomolecule has a molecular weight of from about 0.5 kilodaltons to about 100 kilodaltons.

49. A method for increasing the extent of covalent binding of a biomolecule to $\alpha_2$-macroglobulin to form a biomolecule-$\alpha_2$-macroglobulin complex prepared in accordance with claim 22, wherein prior to reaction of said biomolecule with said nucleophile-activated $\alpha$2-macroglobulin, said biomolecule is treated with a mild oxidizing agent.

50. The method of claim 49 wherein said oxidizing agent is N-chlorobenzenesulfonamide.

51. A stable complex comprising at least one intact biomolecule having a nucleophilic group and activated $\alpha_2$-macroglobulin having a bait region, wherein said intact biomolecule having a nucleophilic group is bound to said activated $\alpha_2$-macroglobulin through a bond consisting of said nucleophilic group covalently bound to a $\gamma$-glutamyl group of a cleaved thiol ester of said activated $\alpha_2$-macroglobulin, said complex produced by a process comprising the steps of:

i) activating $\alpha_2$-macroglobulin to form activated $\alpha_2$-macroglobulin by incubation of $\alpha_2$-macroglobulin with a nucleophilic compound in the absence of a proteinase capable of cleaving said biomolecule having a nucleophilic group and said bait region;

ii) removing excess said nucleophilic compound; and iii) incubating said activated $\alpha_2$-macroglobulin with said biomolecule having a nucleophilic group for a period of time sufficient to form said complex.

52. The stable complex of claim 51 wherein said biomolecule is selected from the group consisting of peptides, proteins, carbohydrates, cytokines, growth factors, hormones, enzymes, toxins, anti-sense RNA, drugs, oligonucleotides, lipids, DNA, antigens, immunogens, allergens, and combinations thereof.

53. The stable complex of claim 52 wherein said antigen is selected from the group consisting of HIV antigens, hepatitis virus antigens, peptides thereof, fragments thereof, hybrid peptides thereof, chimeric peptides thereof, and hybrid synthetic peptides thereof.

54. The stable complex of claim 53 wherein said HIV antigens or fragments thereof comprises gp120, gp160, or a fragment thereof.

55. The stable complex of claim 53 wherein said hepatitis virus antigens of fragments thereof comprises HbsAg or a fragment thereof.

56. The stable complex of claim 52 wherein said biomolecule is selected from the group consisting of KQIINMWQEVGKAMYACTRPNYNKRKRIHIGPGRAFYTTK (SEQ ID NO:1); KQIINMWQEVGKAMYACTRPNNNTRKSIRIQRGPGRAFVTI (SEQ ID NO:2); CTTPAQGNSMFPSCCCTKPTDGNC (SEQ ID NO:3); and TRILTIPQSLDSCTKPTDGNC (SEQ ID NO:4).

57. The stable complex of claim 51 wherein said biomolecule has a molecular weight of from about 0.5 kilodaltons to about 100 kilodaltons.

58. The stable complex of claim 51 wherein said nucleophilic compound has the formula $RNH_2$, wherein R is selected from the group consisting of hydrogen and an alkyl group of 1 to 6 carbon atoms.

59. The stable complex of claim 58 wherein said nucleophilic compound is selected from the group consisting of ammonia, methylamine, ethylamine, and combinations thereof.

60. The stable complex of claim 51 wherein said incubating of said nucleophile-activated $\alpha_2$-macroglobulin with said biomolecule having a nucleophilic group is carried out at a temperature ranging from about 35° C. to about 55° C.

61. The stable complex of claim 60 wherein said incubation step is carried out at a temperature ranging from about 37° C. to about 50° C., and a period of time ranging from about 1 hour to about 24 hours.

62. The stable complex of claim 61 wherein the temperature and time ranges of said incubation are selected from a temperature of about 37° C. for about 24 hours, and a temperature of about 50° C. from about 1 to about 5 hours.

63. The stable complex of claim 51 wherein said stable complex is an immunogen, an antigen presentation complex, or a vaccine.

* * * * *

SEQUENCE LISTING

<160> NUMBER OF SEQ ID NOS: 4

<210> SEQ ID NO 1
<211> LENGTH: 40
<212> TYPE: PRT
<213> ORGANISM: HIV

<400> SEQUENCE: 1

```
Lys Gln Ile Ile Asn Met Trp Gln Glu Val Gly Lys Ala Met Tyr Ala
 1               5                  10                  15

Cys Thr Arg Pro Asn Tyr Asn Lys Arg Lys Arg Ile His Ile Gly Pro
                20                  25                  30

Gly Arg Ala Phe Tyr Thr Thr Lys
                35                  40
```

<210> SEQ ID NO 2
<211> LENGTH: 41
<212> TYPE: PRT
<213> ORGANISM: HIV

<400> SEQUENCE: 2

```
Lys Gln Ile Ile Asn Met Trp Gln Glu Val Gly Lys Ala Met Tyr Ala
 1               5                  10                  15

Cys Thr Arg Pro Asn Asn Asn Thr Arg Lys Ser Ile Arg Ile Gln Arg
                20                  25                  30

Gly Pro Gly Arg Ala Phe Val Thr Ile
                35                  40
```

<210> SEQ ID NO 3
<211> LENGTH: 24
<212> TYPE: PRT

-continued

```
<213> ORGANISM: HBSAG

<400> SEQUENCE: 3

Cys Thr Thr Pro Ala Gln Gly Asn Ser Met Phe Pro Ser Cys Cys Cys
 1               5                  10                  15

Thr Lys Pro Thr Asp Gly Asn Cys
            20

<210> SEQ ID NO 4
<211> LENGTH: 21
<212> TYPE: PRT
<213> ORGANISM: HBSAG

<400> SEQUENCE: 4

Thr Arg Ile Leu Thr Ile Pro Gln Ser Leu Asp Ser Cys Thr Lys Pro
 1               5                  10                  15

Thr Asp Gly Asn Cys
            20
```